United States Patent
Ross et al.

(10) Patent No.: US 12,076,461 B2
(45) Date of Patent: Sep. 3, 2024

(54) USE OF RESECTED LIVER SERUM FOR WHOLE LIVER-ENGINEERING

(71) Applicants: Miromatrix Medical Inc., Eden Prairie, MN (US); Mayo Foundation for Medical Education and Research, Rochester, MN (US)

(72) Inventors: Jeffrey Ross, Chaska, MN (US); Anne Young, New Brighton, MN (US); Allie Haarstad, Bloomington, MN (US); Scott Nyberg, Rochester, MN (US)

(73) Assignees: Miromatrix Medical Inc., Eden Prairie, MN (US); Mayo Foundation for Medical Education & Research, Mayo Medical Ventures, Rochester, MN (US)

( * ) Notice: Subject to any disclaimer, the term of this patent is extended or adjusted under 35 U.S.C. 154(b) by 0 days.

(21) Appl. No.: 17/665,955

(22) Filed: Feb. 7, 2022

(65) Prior Publication Data

US 2022/0323645 A1    Oct. 13, 2022

Related U.S. Application Data

(63) Continuation of application No. 15/697,078, filed on Sep. 6, 2017, now Pat. No. 11,278,643.

(60) Provisional application No. 62/383,772, filed on Sep. 6, 2016.

(51) Int. Cl.
| | | |
|---|---|---|
| A61L 27/36 | (2006.01) | |
| A61L 27/24 | (2006.01) | |
| A61L 27/38 | (2006.01) | |
| C12N 5/071 | (2010.01) | |

(52) U.S. Cl.
CPC .......... *A61L 27/3616* (2013.01); *A61L 27/24* (2013.01); *A61L 27/3604* (2013.01); *A61L 27/3633* (2013.01); *A61L 27/3683* (2013.01); *A61L 27/3804* (2013.01); *A61L 27/3808* (2013.01); *A61L 27/3834* (2013.01); *A61L 27/3839* (2013.01); *C12N 5/0671* (2013.01); *A61L 2430/28* (2013.01); *C12N 2500/84* (2013.01); *C12N 2533/90* (2013.01)

(58) Field of Classification Search
None
See application file for complete search history.

(56) References Cited

U.S. PATENT DOCUMENTS

| | | |
|---|---|---|
| 1,995,970 A | 3/1935 | Lowrance |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,951,828 A | 9/1960 | Zeile |
| 3,531,561 A | 9/1970 | Trehu |
| 3,545,221 A | 12/1970 | Swenson |
| 3,639,084 A | 2/1972 | Goldhaber |
| 4,083,066 A | 4/1978 | Schmitz |
| 4,801,299 A | 1/1989 | Brendel |
| 5,336,616 A | 8/1994 | Livesey |
| 6,376,244 B1 | 4/2002 | Atala |
| 6,379,963 B2 | 4/2002 | Haverich |
| 6,416,995 B1 | 7/2002 | Wolfinbarger |
| 6,432,712 B1 | 8/2002 | Wolfinbarger, Jr. |
| 6,479,064 B1 | 11/2002 | Atala |
| 6,689,161 B2 | 2/2004 | Chen |
| 6,749,064 B1 | 6/2004 | Alrey |
| 6,753,181 B2 | 6/2004 | Atala |
| 6,962,814 B2 | 11/2005 | Mitchell |
| 6,970,427 B2 | 11/2005 | Ranta-Aho |
| 7,311,904 B2 | 12/2007 | Hariri |
| 7,354,749 B2 | 4/2008 | Fisher |
| 8,445,260 B2 | 5/2013 | Owen |
| 8,470,520 B2 | 6/2013 | Ott |
| 9,290,738 B2 | 3/2016 | Ross |
| 9,334,479 B2 | 5/2016 | Herrera Sanchez |
| 9,974,814 B2 | 5/2018 | Katane |
| 10,213,525 B2 | 2/2019 | Ross |
| 10,220,056 B2 | 3/2019 | Ott |
| 10,441,609 B2 | 10/2019 | Ott |
| 2001/0049138 A1 | 12/2001 | Dennis |
| 2002/0081728 A1 | 6/2002 | Haverich |
| 2003/0087428 A1 | 5/2003 | Wolfinbarger, Jr. |
| 2003/0096407 A1 | 5/2003 | Atala |
| 2003/0124099 A1 | 7/2003 | Atala |
| 2003/0215945 A1 | 11/2003 | Atala |
| 2003/0228692 A1 | 12/2003 | Goldstein |
| 2004/0176855 A1 | 9/2004 | Badylak |

(Continued)

FOREIGN PATENT DOCUMENTS

| | | |
|---|---|---|
| AU | 2006282783 B2 | 3/2007 |
| AU | 2013224686 B2 | 9/2013 |

(Continued)

OTHER PUBLICATIONS

Badylak, S. F., et al., Whole-Organ Tissue Engineering: Decellularization and Recellularization of Three-Dimensional Matrix Scaffolds, Annu Rev Biomed Eng., vol. 13, Aug. 15, 2011, 27-53.

Caralt M. et al., Optimization and Critical Evaluation of Decellularization Strategies to Develop Renal Extracellular Matrix Scaffolds as Biological Templates for Organ Engineering and Transplantation. American Journal of Transplantation, vol. 15, 64-75 (2015).

Chronic Kidney Disease in the United States, (US Department of Health and Human Services, Centers for Disease Control and Prevention, Atlanta, GA, 2019). Organ Procurement and Transplantation Network Website. Published 2019. Accessed 2019.

(Continued)

*Primary Examiner* — Teresa E Knight
(74) *Attorney, Agent, or Firm* — Greenberg Traurig, LLP

(57) ABSTRACT

The disclosure provides a method of using blood or fractions thereof, e.g., serum, obtained from a mammal subjected to liver surgery, for example, obtained following a partial hepatectomy, to increase the engraftment, proliferation and/or functionality of cells on a biocompatible scaffold.

13 Claims, 1 Drawing Sheet

(56) References Cited

U.S. PATENT DOCUMENTS

| | | |
|---|---|---|
| 2004/0187877 A1 | 9/2004 | Badylak |
| 2005/0084512 A1 | 4/2005 | Denizeau |
| 2005/0249816 A1 | 11/2005 | Atala |
| 2005/0260612 A1 | 11/2005 | Padmini |
| 2007/0020610 A1 | 1/2007 | Sherley |
| 2007/0059293 A1 | 3/2007 | Atala |
| 2007/0248638 A1 | 10/2007 | Van Dyke |
| 2008/0058956 A1 | 3/2008 | Badylak |
| 2009/0169525 A1 | 7/2009 | Anversa |
| 2009/0202977 A1 | 8/2009 | Ott |
| 2010/0093066 A1 | 4/2010 | Taylor |
| 2011/0059152 A1 | 3/2011 | Atala |
| 2012/0064537 A1 | 3/2012 | Ross |
| 2012/0183944 A1 | 7/2012 | Taylor |
| 2013/0109088 A1 | 5/2013 | Ott |
| 2013/0156744 A1 | 6/2013 | Taylor |
| 2013/0344599 A1 | 12/2013 | Ott |
| 2014/0227734 A1 | 8/2014 | Hariyama |
| 2015/0238656 A1 | 8/2015 | Orlando |
| 2016/0030637 A1 | 2/2016 | Ross |
| 2016/0030638 A1 | 2/2016 | Ross |
| 2016/0095956 A1 | 4/2016 | Ansari |
| 2017/0101618 A1 | 4/2017 | Kamen |
| 2018/0064848 A1 | 3/2018 | Ross |
| 2018/0325102 A1 | 11/2018 | Chin |
| 2019/0343877 A1 | 11/2019 | Ott |

FOREIGN PATENT DOCUMENTS

| | | |
|---|---|---|
| CN | 1615162 A | 5/2005 |
| CN | 101066477 A | 11/2007 |
| CN | 101272815 A | 9/2008 |
| CN | 101272815 B | 9/2008 |
| CN | 101366978 A | 2/2009 |
| CN | 102477172 A | 5/2012 |
| CN | 102861359 A | 1/2013 |
| EP | 1246903 A1 | 10/2002 |
| EP | 1928519 B1 | 6/2008 |
| EP | 2431063 A2 | 3/2012 |
| EP | 2431063 B1 | 3/2012 |
| EP | 2611472 B1 | 7/2013 |
| EP | 2965769 A1 | 1/2016 |
| ES | 2384721 T3 | 7/2012 |
| JP | S5516016 A | 2/1980 |
| JP | H06261933 A | 9/1994 |
| JP | H1176400 A | 3/1999 |
| JP | 2000004870 A | 1/2000 |
| JP | 2004167236 A | 6/2004 |
| JP | 2005509495 A | 4/2005 |
| JP | 2007222391 A | 9/2007 |
| JP | 2008541717 A | 11/2008 |
| JP | 2009505752 A | 2/2009 |
| JP | 2012522511 A | 9/2012 |
| JP | 2013536738 A | 9/2013 |
| JP | 2015094591 A | 5/2015 |
| JP | 6089062 B2 | 9/2015 |
| JP | 2015164549 A | 9/2015 |
| JP | 2016039903 A | 3/2016 |
| JP | 2016513465 A | 5/2016 |
| JP | 2016521611 A | 7/2016 |
| JP | 2017038948 A | 2/2017 |
| MX | 34363 A | 11/2016 |
| RU | 2463081 C2 | 10/2009 |
| RU | 2011143730 A | 5/2013 |
| RU | 2611361 C2 | 10/2014 |
| WO | WO-9608213 A1 | 3/1996 |
| WO | WO-0148153 A1 | 7/2001 |
| WO | WO-0149210 A1 | 7/2001 |
| WO | WO-0224244 A1 | 3/2002 |
| WO | WO-0240630 A2 | 5/2002 |
| WO | WO-0249681 A1 | 6/2002 |
| WO | WO-02063962 A1 | 8/2002 |
| WO | WO-03039610 A1 | 5/2003 |
| WO | WO-03043674 A1 | 5/2003 |
| WO | WO-2004054571 A1 | 7/2004 |
| WO | WO-2004080501 A1 | 9/2004 |
| WO | WO-2004100832 A1 | 11/2004 |
| WO | WO-2005118014 A2 | 12/2005 |
| WO | WO-2006033415 A1 | 3/2006 |
| WO | WO-2006122533 A2 | 11/2006 |
| WO | WO-2007025233 A1 | 3/2007 |
| WO | WO-2010120539 A2 | 10/2010 |
| WO | WO-2011031484 A2 | 3/2011 |
| WO | WO-2012005760 A1 | 1/2012 |
| WO | WO-2012031162 A1 | 3/2012 |
| WO | WO-2014168719 A1 | 10/2014 |
| WO | 2018048899 A1 | 3/2018 |
| WO | WO-2018071354 A1 | 4/2018 |

OTHER PUBLICATIONS

Cukierman, et al., Taking Cell-Matrix Adhesions to the Third Dimension, Science, Nov. 23, 2001, vol. 294(5547), 1708-12.

Elhamahmi et al., Kidney Discard Rates in the United States During American Transplant Congress Meetings. Transplant Direct, vol. 5, e412 (2019).

Golriz M. et al., Pig Kidney Transplantation: An Up-to-Date Guideline. Eur Surg Res, vol. 49, 121-129 (2012).

International Search Report and Written Opinion for PCT/US2020/063460, mailed Apr. 9, 2021.

Jay, Steven M, et al., Engineering of Multifunctional Gels Integrating Highly Efficient Growth Factor Delivery with Endothelial Cell Transplantation, The FASEB journal, vol. 22, No. 8, (Apr. 16, 2008), 2949-2956.

Kim et al., Gene-Edited Human Kidney Organoids Reveal Mechanisms of Disease in Podocyte Development. Stem Cells, vol. 35, 2366-2378 (2017).

Leuning et al., Vascular bioengineering of scaffold derived from human discarded transplant kidneys using human pluripotent stem cell-derived endothelium, American Journal of Transplant Surgeons, 2019, vol. 19, p. 1928-1343.

Little, M. H., Mammalian Kidney Development: Principles, Progress, and Projections. Cold Spring Harbor, Perspectives in Biology, vol. 4, a008300 (2012).

Lovett, Michael, et al., Vascularization Strategies for Tissue Engineering, Tissue Engineering Part B: Reviews, vol. 15, No. 3, (Sep. 1, 2009), 353-370.

Mcmahon, A. P., in Current topics in developmental biology. (Elsevier, 2016), vol. 117, pp. 31-64.

Miyoshi, T. et al., Kidney Organoids in Translational Medicine: Disease Modeling and Regenerative Medicine. Developmental Dynamics, (2019).

Molema G. et al., Vascular Heterogeneity in the Kidney. Semin Nephrol, vol. 32, 145-155 (2012).

Morizane R. et al., Nephron Organoids Derived from Human Pluripotent Stem Cells Model Kidney Development and Injury. Nat Biotechnol, vol. 33, 1193-1200 (2015).

Morizane, et al., Generation of Nephron Progenitor Cells and Kidney Organoids from Human Pluripotent Stem Cells. Nat Protoc, vol. 12, 195-207 (2017).

Nakayama, K. H et al., Decellularized Rhesus Monkey Kidney as a Three-Dimensional Scaffold for Renal Tissue Engineering. Tissue Engineering Part A, vol. 16, 2207-2216 (2010).

PCT/US2020/024052 International Search Report dated Jun. 12, 2020.

Pellegata, et al., Whole Organ Tissue Vascularization: Engineering the Tree to Develop the Fruits. Front Bioeng Biotechnol, vol. 6, 56 (2018).

Song et al., Regeneration and Experimental Orthotopic Transplantation of a Bioengineered Kidney. Nature Medicine Advance Online Publication, Received Sep. 4, 2012; accepted Feb. 11, 2013; published online Apr. 14, 2013, (2013), 1-8.

Takasoto, M. et al., Generation of Kidney Organoids from Human Pluripotent Stem Cells. Nat Protoc, vol. 11, 1681-1692 (2016).

Uzarski et al., Epithelial Cell Repopulation and Preparation of Rodent Extracellular Matrix Scaffolds for Renal Tissue Development. Journal of Visualized Experiments, e53271, (2015).

(56) References Cited

OTHER PUBLICATIONS

Uzarski J. S. et al., Essential Design Considerations for the Resazurin Reduction Assay to Noninvasively Quantify Cell Expansion Within Perfused Extracellular Matrix Scaffolds. Biomaterials, vol. 129, 163-175 (2017).
Wallis, J. M. et al., Comparative Assessment of Detergent-Based Protocols for Mouse Lung De-Cellularization and Re-Cellularization. Tissue Engineering Part C: Methods, vol. 18, 420-432 (2012).
Wang, Y. et al., Method for Perfusion Decellularization of Porcine Whole Liver and Kidney for use as a Scaffold for Clinical-Scale Bioengineering Engrafts. Xenotransplantation, vol. 22, 48-61 (2015).
Wu, H. et al., Comparative Analysis and Refinement of Human PSC-Derived Kidney Organoid Differentiation with Single-Cell Transcriptomics. Cell Stem Cell, vol. 23, 869-881.e868 (2018).
Yu, Y. et al., Decellularized Kidney Scaffold-Mediated Renal Regeneration. Biomaterials, vol. 35, 6822-6828 (2014).
Abbott, There's a big difference between a flat layer of cells and a complex, three-dimensional tissue. But until recently, many biologists have glossed over this fact. Alison Abbott discovers what they've been missing., Nature, vol. 424, 2003, p. 870-872.
Peloso et al., Creation and implantation of acellular rat renal ECM based scaffolds, Organogenesis, vol. 11, p. 58-74, 2015.
Arenas-Herrera et al., Decellularization for whole organ bioengineering, Biomedical Materials, 2013, vol. 8, No. 1, p. 1-9.
Du et al., Functional Kidney Bioengineering with Pluripotent Stem-Cell-Derived Renal Progenitor Cells and Decellularized Kidney Scaffolds, Adv. Healthcare Mater, 2016, vol. 5, p. 2080-2091.
Jackson et al., The lymphatics revisited: new perspectives from the hyaluronan receptor LYVE-1, Trends in Cardiovascular Medicine, 2003, vol. 13, No. 1, p. 1-7.
Mazza et al., Decellularized human liver as a natural 3D-scaffold for liver bioengineering and transplantation, Scientific Reports, 2015, vol. 5, p. 1-15.
Mussbach et al., Bioengineered Livers: A New Tool for Drug Testing and a Promising Solution to Meet the Growing Demand for Donor Organs, European Surgical Research, 2016, vol. 57, p. 224-239.
Serna-Marquez et al., Fibrillar Collagen Type I Participates in the Survival and Aggregation of Primary Hepatocrytes Cultured in Soft Hydrogels, Biometrics, 2020, vol. 5, No. 2, p. 1-21.
Zhang et al., A decade of progress in liver regenerative medicine, Biomaterials, 2018, vol. 157, p. 161-176.
Alberts et al. Molecular biology of the cell (third edition) Garland Publishing, New York and London, (1994): 971-977.
Atala et al. Tissue-engineered autologobladders for patients needing cystoplasty. The Lancet, vol. 367, 2006, p. 1241-1246.
ATALA Recent developments in tissue engineering and regenerative medicine. Current Opinion in Pediatrics 18.2 (2006): 167-171.
Bader et al., Tissue Engineering of Heart Valves-Human Endothelial Cell Seeding of Detergent Acellularized Porcine Valves. European Journal of Cardio-Thoracic Surgery, 14.3 1998): 279-284.
Badylak. Xenogeneic extracellular matrix as a scaffold for tissue reconstruction. Transpl Immunol. 12(3-4), (Apr. 2004): 367-77.
Baertschiger et al. Xenotransplantation Literature Update Nov.-Dec. 2005 Xenotransplantation 13, (2006): 96-99.
Bao, J., et al., Construction of a portal implantable functional tissue-engineered liver using perfusion-decellularized matrix and hepatocytes in rats. Cell Transplant, 2011. 20(5): p. 753-766.
Bao, J., et al., Hemocompatibility improvement of perfusion-decellularized clinical-scale liver scaffold through heparin immobilization. Sci Rep, 2015, vol. 5.
Baptista et al. A Novel Whole Organ Bioscaffold for Tissue Engineering and Regenerative Medicine Applications. The FASEB Journal, 21 (Meeting Abstract Supplement), Database Biosis Abstract, (2007).
Baptista et al. The Use of Whole Organ Decellularization for the Generation of a Vascularized Liver Organoid. Hepatology, 53(2), (2011), 604-617.
Baptista, P. M, et al., Human Liver Bioengineering Using a Whole Liver Decellularized Bioscaffold. Methods Mol Biol., 1001, (2013): 1 page (Abstract Only).
Barakat et al., Use of Decellularized Porcine Liver for Engineering Humanized Liver Organ. Journal of Surgical Research, vol. 173(11), (2012).
Batchelder et al. Natural Scaffolds for Renal Differentiation of Human, Human Embryonic Stem Cells for Kidney Tissue Engineering. PLOS One, 10(12); 2015.
Bauer et al. hDAF porcine cardiac xenograft maintains cardiac output after orthotopic gtransplantation into a baboon—a perioperative study. Xenotransplantation, Nov. 2005. 12(6), (2005): 444-9.
Bodnar et al., Damage of Porcine Aortic Valve Tissue Caused by the Surfactant Sodiumdodecylsulphate. Thorac. cardiovasc. Surg. 34, (1986): 82-85.
Bonandrini et al., Recellularization of Well-Preserved Acellular Kidney Scaffold using Embryonic Stem Cells. Tissue Engineering Part A, vol. 20, 1486-1498 (2014).
Bonvillain, R. W, et al., A Nonhuman Primate Model of Lung Regeneration: Detergentmediated Decellularization and Initial in Vitro Recellularization with Mesenchymal Stem Cells. Tissue Eng Part A., 18(23-24), (Dec., 2012): 1 page (Abstract Only).
Borschel et al. Contractile skeletal muscle tissue-engineered on an acellular scaffold. Plastic and reconstructive surgery 113.2 (2004): 595-602.
Brendel et al. The acellular perfused kidney: a model for basement membrane permeability. Biology and Chemistry of Basement Membranes, Nicholas A Kefalides, author; New York : Academic Press, (1978), 177-193.
Brodie, The perfusion of surviving organs. The Journal of Physiology, vol. 29(3) (1903): 266-275.
Carreira C, et al., LYVE-1 is not Restricted to the Lymph Vessels: Expression in Normal Liver Blood Sinusoids and Down-Regulation in Human Liver Cancer and Cirrhosis, Cancer Res. Nov. 15, 2001;61(22):8079-84.
Cartmell et al. Development of Cell-Seeded Patellar Tendon Allografts for Anterior Cruciate Ligament Reconstruction. Tissue Eng. 10, (2004), 1065-1075.
Cebotari et al. Construction of Autologous Human Heart Valves Based on an Acellular Allograft Matrix. Circulation 106 (suppl 1), (2002), 1-63 to 1-68.
Chen et al. Acellular collagen matrix as a possible off the shelf biomaterial for urethral repair. Urology 54, (1999), 407-410.
Chen et al. Experimental and clinical experience using tissue regeneration for urethral reconstruction. World J. Urol. 18, (2000), 67-70.
Chen et al., Process Development of an Acellular Dermal Matrix (ADM) for Biomedical Applications. Biomaterials 25, (2004), 2679-2686.
Choi, et al., Changes in Ultrasonic Properties to Liver Tissue in Vitro During Heating-Cooling Cycle Concomitant With Thermal Coagulation, Jun. 23, 2011 (Jun. 23, 2011), Ultrasound in Med. & Biol., vol. 37, No. 12, pp. 2000-2012.
Conconi et al. Homologomuscle acellular matrix seeded with autologomyoblasts as a tissue-engineering approach to abdominal wall-defect repair. Biomaterials 26, (2005), 2567-2574.
Courtman et al., Development of a pericardial Acellular Matrix Biomaterial: Biochemical and Mechanical Effects of Cell Extraction. J Biomed Materi Res., 28(6), (1994), 655-666.
Crapo et al., An Overview of Tissue and Whole Organ Decellularization Processes. Biomaterials, 32, (2011), 3233-3243.
Czyz et al. Embryonic stem cell differentiation: The role of extracellular factors. Differentiation, 68, (2001), 167-174.
Dahl et al., Decellularized Native and Engineered Arterial Scaffolds for Transplantation. Cell Transplant 12, (2003), 659-666.
Daly, A. B, et al., Initial Binding and Recellularization of Decellularized Mouse Lung Scaffolds with Bone Marrow-Derived Mesenchymal Stromal Cells. Tissue Eng Part A., vol. 18(1-2), (Jan. 2012).
Database Accession No. PREV200300571885 and Abstract.
Davis et al., Endothelial Extracellular Matrix: Biosynthesis, Remodeling, and Functions During Vascular Morphogenesis and Neovessel Stabilization. Circ. Res. 97, (2005), 1093-1107.

(56) References Cited

OTHER PUBLICATIONS

Dellgren et al., Eleven Years' Experience with the Biocor Stentless Aortic Bioprsthesis: Clinical and Hemodynamic Follow-up with Long-Term Relative Survival Rate. Eur. J. Cardiothorac. Surg. 22, (2002), 912-921.
Den Butter, G., Saunder, A., Marsh, D.C. et al., Comparison of solutions for preservation of the rabbit liver as tested by isolated perfusion, Transpl Int 8, 466-471 (1995).
Deng et al. Destination Mechanical circulatory Support: Proposal for Clinical Standards. J. Heart Lung Transplant, vol. 22, (2003), 365-369.
Destefani et al., Advances in the Knowledge about Kidney Decellularization and Repopulation. Frontiers in Bioengineering and Biotechnology, 2017, vol. 5, Article 34.
Deyl et al. Steric hindrances in protein permeation through the basement membrane studied in acellular kidney. Physiologia Bohemoslovaca 36.5 (1987): 425-434.
Dhawan et al., Human hepatocyte transplantation: current experience and future challenges. Nat Rev Gastroenterol Hepatol, 2010. 7(5): p. 288-98.
Do, et al., 3D Printing of Scaffolds for Tissue Regeneration Applications. Advanced Healthcare Materials, 2015. 4(12): p. 1742-1762.
Doi, R., et al., Transplantation of Bioengineered Rat Lungs Recellularized with Endothelial and Adipose-Derived Stromal Cells. Scientific Reports, 2017, p. 1-15.
Downing et al., Technical Assessment of the First 20 Years of Research Using Mouse Embryonic Stem Cell Lines. Stem Cells, vol. 22, (2004), 1168-1180.
Drug Metabolism and Liver Biology. PloS One. Jan. 29, 2018; vol. 13, No. 1; pp. 1-23.
Duhaut et al., Approximately 150 Nucleotides from the 5" End of an Influenza A Segment 1 Defective Virion RNA are Needed for Genome Stability During Passage of Defective Virus in Infected Cells. Virology, vol. 275(2), (2000): 278-285.
Elkins et al. Decellularized Human Valve Allografts. Ann. Thorac. Surg. 71 (suppl 5), (2001): S428-S432.
Emerich et al., Targeted nanoparticle-based drug delivery and diagnosis, Journal of Drug Targeting, 15:3, 163-183 (2007).
Engbers-Buijtenhuijs et al., Biological Characterisation of Vascular Grafts Cultured in a Bioreactor. Biomaterials, vol. 27, (2006), 2390-2397.
Eschenhagen et al., Engineering Myocardial Tissue. Circulation Research, vol. 97.12 (2005): 1220-1231.
Faulk, D. M, et al., Role of the Extracellular Matrix in Whole Organ Engineering. J Cell Physiol., (Abstract Only): (Dec. 18, 2013): 1 Page.
Firth, John D. et al., Sodium Handling In The Isolated Perfused Kidney Of The Cirrhotic Rat, Clinical Science (1989) 77, 657-661.
Frantz et al. The extracellular matrix at a glance. Cell Science at a Glance, vol. 123, (2010), 4195-4200.
Fridman et al. A Pilot Study to Evaluate the Effects of Perfusion-decellularized Porcine Hepatic-derived Wound Matrix on Difficult-to-heal Diabetic Foot Ulcers. The Official Journal of AAWC, Wounds, A Compendium of Clinical Research and Practice, vol. 29, No. 10, Oct. 2017, (2017), 317-323.
Furuta et al., Pulsatile Cardiac Tissue Grafts using a Novel Three-Dimensional Cell Sheet Manipulation Technique Functionally Integrates with the Host Heart, in Vivo. Circulation Research, vol. 98.5 (2006): 705-712.
Gentile et al., Effects of Post-Hepatectomized Rat Sera on Cultured Cells, Journal of Surgical Oncology, 1969, p. 3-11.
Gerecht-Nir et al., Biophysical Regulation During Cardiac Development and Application to Tissue Engineering. International Journal of Developmental Biology, vol. 50, Nos. 2-3 (2003): 233-243.
Gilbert et al. Decellularization of tissues and organs. Biomaterials 27.19 (2006): 3675-3683.
Gilpin et al., Enhanced Lung Epithelial Specification of Human Induced Pluripotent Stem Cells on Decellularized Lung Matrix. Ann Thorac Surg., vol. 98, (2014): 721-729.

Glossary at stemcells.nih.gov on the World Wide Web and iPS cells.
Goh, S.K. et al., Perfusion-Decellularized Pancreas as a Natural 3D Scaffold for Pancreatic Tissue and Whole Organ Engineering. Biomaterials, vol. 34, 6760-6772 (2013).
Grabow et al., Mechanical and Structural Properties of a Novel Hybrid Heart Valve Scaffold for Tissue Engineering. Artificial Organs, vol. 28.11 (2004): 971-979.
Groetzner, et al., "Results of Pediatric Cardiac Transplantation—Long-Term Results of a 15-Year Experience", Thorac. Cardiov. Surg 53 (Suppl 2), (2005): S149-S154.
Guan et al., The Effective Bioengineering Method of Implantation Decellularized Renal Extracellular Matrix Scaffolds. Oncotaraet, vol. 6(34), (2015): 36126-36138.
Hassanein, W., et al., Recellularization via the bile duct supports functional allogenic and xenogenic cell growth on a decellularized rat liver scaffold. Organogenesis, 2017, vol. 13(1), p. 16-27.
Hohlfeld, et al., Tissue engineered fetal skin constructs for paediatric burns. Lancet 366, (2005): 840-842.
Hopper et al. Acellularization of human placenta with preservation of the basement membrane: a potential matrix for tissue engineering. Annals of plastic surgery 51.6 (2003): 598-602.
Hou et al. Tissue-engineered peripheral nerve grafting by differentiated bone marrow stromal cells. Neuroscience 140, (2006): 101-110.
Huang et al., Regulation of the matrix microenvironments for stem cell engineering and regenerative medicine, Ann Biomed Eng., Apr. 2011; vol. 39, No. 4, p. 1201-1214.
Huang, et al., Enhanced Functional Maturation of Fetal Porcine Hepatocytes in Three-Dimensional Poly-L-Lactic Acid Scaffolds: A Culture Condition Suitable for Engineered Liver Tissues in Large-Scale Animal Studies. Cell Transplant. vol. 15(8-9), (2006): 799-809.
Hudson et al. Engineering an improved acellular nerve graft via optimized chemical processing. Tissue engineering 10.9-10 (2004): 1346-1358.
Hussein, K.H., et al., Heparin-Gelatin Mixture Improves Vascular Reconstruction Efficiency and Hepatic Function in Bioengineered Livers, Acta Biomater, 2016, vol. 38, p. 82-93.
Hussein, Three Dimensional Culture of HepG2 Liver Cells on a Rat Decellurized Liver Matrix for Pharmacological Studies. Journal of Biomedical Materials B: Applied Biomaterials. vol. 1048.2, (2015): 263-273.
Ikeda et al., Growing Bioengineered Teeth from Single Cells: Potential for Dental Regenerative Medicine. Expert Opinion on Biological Therapy, vol. 8(6) (2008): 735-744.
International Application Serial No. PCT/US2017/050278, International Search Report and Written Opinion mailed Dec. 12, 2017.
International Search Report and Written Opinion for PCT/US17/50276 mailed Dec. 12, 2017.
International Search Report dated Aug. 28, 2019 for International Application Serial No. PCT/US19/35449, (4 pages).
Isenberg et al., Small Diameter Artificial Arteries Engineered In Vitro. Circulation Research, vol. 98, (2006): 25-35.
Jawad, et al., Myocardial Tissue Engineering. Br Med Bull., vol. 87, (2008): 31-47.
Juncosa-Melvin, et al., The Effect of Autologous Mesenchymal Stem Cells on the Biomechanics and Histology of Gel-Collagen Sponge Constructs Used for Rabbit Patellar Tendon Repair. Tissue Engineering, vol. 12, (2006), 369-379.
Kang et al. Decellularization technology application in which live reconstruct biological scaffold. National Medical Journal of China, vol. 89.16 (2009): 1135-1138.
Kasimir et al., The Decellularized Porcine Heart Valve Matrix in Tissue Engineering. Platelet Adhesion and Activation, (2005): 562-567.
Keller, Embryonic Stem Cell Differentiation: Emergence of a New Era in Biology and Medicine Genes & Development, vol. 19, (2005): 1129-1155.
Ketchedjian et al., Recellularization of Decellularized Allograft Scaffolds in Ovine Great Vessel Reconstructions. Ann. Thorac. Surg., vol. 79, (2005): 888-896.
Kim, et al., OPTN/SRTR 2016 Annual Data Report: Liver. American Journal of Transplantation, 2018. 18(S1): p. 172-253.

(56) References Cited

OTHER PUBLICATIONS

Kitahara et al., Heterotopic Transplantation of a Decellularized and Recellularized Whole Porcine Heart. Interactive Cardiovascular and Thoracic Surgery, (2016), 571-579.
Knight et al. Tissue Engineering of Cardiac Valves: Re-Seeding of Acellular Porcine Aortic Valve Matrices with human Mesenchymal Progenitor Cells. J. Heart Valve Disease 14, (2005): 806-813.
Ko, et al., Bioengineered Transplantable Porcine Livers with Re-Endothelialized Vasculature. Biomaterials, 2015, vol. 40, p. 72-79.
Kofidis et al. Myocardial restoration and tissue engineering of heart structures. Tissue Engineering (2007): 273-290.
Kojima H, et al., Establishment of Practical Recellularized Liver Graft for Blood Perfusion Using primary Rat Hepatocytes and Liver Sinusoidal Endothelial Cells, American Journal of Transplantation, Jun. 2018;18(6):1351-1359.
Kolker et al. Multilayer Reconstruction of abdominal Wall defects with Acellular Dermal Allograft (AlloDerm) and component Separation. Ann. Plast. Surg. 55, (2005): 36-41.
Kren et al., The Production of a Bio-Engineered Endothelial Intima From Cultured Cells Using Whole Cardiac Cadaveric Extracellular Matrix. Circulation, vol. 116, Database Biosis, (2007).
Lalor, P.F., et al., Human hepatic sinusoidal endothelial cells can be distinguished by expression of phenotypic markers related to their specialised functions in vivo. World Journal of Gastroenterology : WJG, 2006, vol. 12, No. 34, p. 5429-5439.
Langer et al., Tissue Engineering. Science 260 (1993): 920-926.
Lapidot et al., How do Stem Cells Find Their Way Home?, Blood, vol. 106(6), (2005): 1901-1910.
Lee, GraftJacket Augmentation of Chronic Achilles Tendon Ruptures. Orthopedics, vol. 27, 2004, p. 151-153.
Levenberg et al., Engineering Vascularized Skeletal Muscle Tissue. Nat. Biotechnol, vol. 23(7), (2005): 879-884.
L'Heureux et al., Human Tissue-Engineered Blood Vessels for Adult Arterial Revascularization. Nature Medicine, vol. 12(3), (2006): 361-365.
Lichtenberg et al. Flow-Dependent Re-Endothelialization of Tissue-Engineered Heart Valve J. Heart Valve Dis. 15 (2006), p. 287-294.
Lin, et al., Accessing Porcine Liver-Derived Biomatrix for Hepatic Tissue Engineering Tissue Eng., vol. 10, (2004), 1046-1053.
Liu et al., Elastic Fiber Homeostasis Requires Lysyl Oxidase-Like 1 Protein. Nature Genetics, vol. 36(2), (2004): 178.
Liver Regeneration, [online]. (c) 1998-2016 Mayo Foundation for Medical Education and Research, Retrieved from the Internet URL: http://www.mayo.edu/research/centers-programs/center-regenerative-medicine/focus-areas/liver-regeneration.
Lopez, et al., Update on liver transplantation: indications, organ allocation, and long-term care. Mt Sinai J Med, 2006. 73(8): p. 1056-66.
Lu et al., Repopulation of Decellularized Mouse Heart with Human Induced Pluripotent Stem Cell-Derived Cardiovascular Progenitor Cells. Nature Communications, vol. 4 (2013): 1-11.
Mao, S., et al., Sustained In Vivo Perfusion of a Re-Endothelialized Tissue Engineered Porcine Liver. Int J Transplant Res Med, 2017, vol. 3, Issue 1, p. 1-9.
Matsuura et al., Cellular Remodeling of Depopulated Bovine Ureter Used as an Arteriovenous Graft in the Canine Model 1. Journal of the American College of Surgeons, vol. 198, No. 5, 2004, 778-783.
Matthiesen et al., Creating Biocompatible 3-D Scaffolds for Engineering Cardiovascular Tissues: Heart, Lung, and Kidney. Circulation, 116 (Meeting Abstract Supplement), Database Biosis, ( 2007), Abstract 428.
Matthiesen et al., Large Solid Organ Perfusion Decellularization—A Start for Human-Sized Tissue Scaffolds ??, Circulation, 116 (Meeting Abstract Supplement), Database Biosis, 2007.
Mazetti, Samanta et al., Molecular Anatomy of the Cerebral Micro Vessels in the Isolated Guinea-Pig Brain, Brain Research. 999, 81-90, 2004.
Mazza, G., et al., Liver tissue engineering: From implantable tissue to whole organ engineering. Hepatol Commun, 2018. 2(2): p. 131-141.

Mcfetridge et al., Preparation of Porcine Carotid Arteries for Vascular Tissue Engineering Applications. Journal of Biomedical Materials Research Part A, vol. 70.2 (2004): 224-234.
Mei, J., et al., The angiogenesis in decellularized scaffold-mediated the renal regeneration. Oncotarget, 2016, vol. 7, Issue 19, p. 27085-27093.
Mirmalek-Sani, S.H., et al., Immunogenicity of Decellularized Porcine Liver for Bioengineered Hepatic Tissue. The American Journal of Pathology, 2013. 183(2): p. 558-565.
Miromatrix Presents Progress on Engineering a Transplantable Liver at the Liver Meeting in Washington DC. Oct. 20, 2017 [retrieved on Aug. 1, 2019]. https://www.miromatrix.com/newsroom/2017/10/20/miromatrix-presents-progress-onengineering-a-transplantable-liver-at-the-liver-meeting-in-washington-dc: pp. 1-4:p. 2, paragraph 2.
Mirsadraee et al., Development and Characterization of an Acellular Human Pericardia! Matrix for Tissue Engineering. Tissue Engineering, vol. 12(4), (2006): 763-773.
Miyagawa et al., Tissue Cardiomyoplasty Using Bioengineered Contractile Cardiomyocyte Sheets to Repair Damaged Myocardium: Their Integration with Recipient Myocardium. Transplantation, vol. 80(11) (2005): 1586-1595.
Moini, Maryam et al., Review on immunosuppression in liver transplantation, World Journal of Hepatology vol. 7,10 (2015): 1355-68.
Munoz-Elias et al. Marrow Stromal Cells, Mitosis, and Neuronal Differentiation: Stem Cell and Precursor Functions. Stem Cells, vol. 21(4) (Jul. 2003), 437-448.
Naito et al. Three-dimensional cardiac tissue engineering using a thermo-responsive artificial extracellular matrix. ASAIO J, 2004, vol. 50(4), p. 344-8, 2017.
Navarro-Tableros et al. Recellularization of Rat Liver Scaffolds by Human Liver Stem Cells. Tissue Engineering: Part A, vol. 21, Nos. 11 and 12, (2015), 1929-1939.
Nicolas et al., Cell Therapy in Chronic Liver Disease. Current opinion in gastroenterology, 2016. 32(3): p. 189-194.
Nicolas, C.T., et al., Liver Regenerative Medicine: From Hepatocyte Transplantation to Bioartificial Livers and Bioengineered Grafts. Stem cells (Dayton, Ohio), 2017. 35(1): p. 42-50.
Niklason et al., Functional Arteries Grown in Vitro. Science, vol. 284, (1999), 489-493.
Nyberg, S.L., et al., Cytotoxic immune response to a xenogeneic bioartificial liver. Cell Transplant, 2004, vol. 13, p. 783-791.
Ohashi, Kazuo, et al., Stability and Repeat Regeneration Potential of the Engineered Liver Tissues under the Kidney Capsule in Mice. Cell Transplantation, vol. 14(9), (Oct. 1, 2005): 621-627.
Oliver et al. Dermal Collagen Implants. Biomaterials 1, (1982), 38-40.
Oswald et al., Mesenchymal Stem Cells can be Differentiated Into Endothelial Cells In Vitro. Stem Cells, vol. 22(3), (2004), 377-384.
Ott, et al., Perfusion-Decellularized Matrix: Using Nature's Platform to Engineer a Bioartificial Heart. Nat Med. 2008, p. 1-9. Advance Online Publication.
Ott, H. C. et al., Regeneration and Orthotopic Transplantation of a Bioartificial Lung. Nature Medicine, vol. 16, 927-934 (2010).
Ott, H. C., et al., Cell-Based Cardiovascular Repair. Basic Res Cardiol, vol. 100, (2005): 504-517.
Park et al. A novel composite scaffold for cardiac tissue engineering. In Vitro Cellular & Developmental Biology—Animal, vol. 41(7), (2005): 188-196.
Park et al., Bioartificial Liver Systems: Current Status and Future Perspective. J Biosci Bioeng., Apr. 2005, vol. 99(4), p. 311_319.
PCT/US/2011/050266 International Search Report and Written Opinion dated Jan. 23, 2012.
PCT/US2006/033415 International Search Report and Written Opinion dated Dec. 21, 2006.
PCT/US2010/029463 International Search Report and Written Opinion dated Dec. 20, 2010.
PCT/US2010/046644 International Search Report and Written Opinion dated Jun. 22, 2011.
Peery, A.F., et al., Burden of gastrointestinal disease in the United States: 2012 update. Gastroenterology, 2012. 143(5): p. 1179-87. e1-3.

(56) References Cited

OTHER PUBLICATIONS

Perry et al., Clinical Scale Expansion of Human Pluripotent Stem Cells, Blood, vol. 106(11), (2005), Abstract Only.
Peters et al., Organ Weights and Water Levels of the Rat following Reduced Food Intake. The Journal of Nutrition, vol. 90, (1966), 354-360.
Petersen et al., Tissue-Engineered Lungs for in Vivo Implantation. Science, vol. 329, 538-541 (2010).
Petro, et al., An in Vivo Analysis of Miromesh—A Novel Porcine Liver Prosthetic Created by Perfusion Decellularization. Journal of Surgical Research, vol. 201, (2016), 29-37.
Phillips et al. Neural Tissue Engineering: A Self-Organizing Collagen Guidance Conduit Tissue Engineering, vol. 11, (2005), 1611-1617.
Philp et al., Complex Extracellular Matrices Promote Tissue-Specific Stem Cell Differentiation, Stem cells, vol. 23(2), 288-296, 2005.
Powers et al., Functional Behavior of Primary Rat Liver Cells in a Three-Dimensional Perfused Microarray Bioreactor. Tissue Engineering, vol. 8(3), (2002), 499-513.
Radisic et al., Mathematical Model of Oxygen Distribution in Engineered Cardiac Tissue with Parallel Channel Array Perfused with Culture Medium Containing Oxygen Carriers. American Journal of Physiology—Heart and Circulatory Physiology, vol. 288(3), (2005), H1278-H1289.
Ren et al., Evaluation of two decellularization methods in the development of a whole-organ decellularized rat liver scaffold. Liver Int. Mar. 2013. vol. 33 No. 3. pp. 448-458.
Rieder et al., Decellularization Protocols of Porcine Heart Valves Differ Importantly in Efficiency of Cell Removal and Susceptibility of the Matrix to Recellularization with Human Vascular Cells. The Journal of Thoracic and Cardiovascular Surgery, vol. 127(2), 2004, p. 399-405.
Robertson et al., Optimizing Recellularization of Whole Decellularized Heart Extracellular Matrix, PLoS ONE, vol. 9(2), (2014), 1-10.
Robertson, Matthew J et al., Recellularization of Rat Liver: An in Vitro Model for Assessing Human Drug Metabolism and Liver Biology, PloS One, vol. 13, 1e0191892, Jan. 29, 2018.
Robinson, et al., Extracellular Matrix Scaffold for Cardiac Repair. Circulation. Aug. 30, 2005, vol. 112(9 Suppl), p. 135-143.
Ross et al., Embryonic Stem Cells Proliferate and Differentiate when Seeded into Kidney Scaffolds. Journal of The American Society of Nephrology, vol. 20, No. 11, (2009), 2338-2347.
Ross et al., Mouse Stem Cells Seeded into Decellularized Rat Kidney Scaffolds Endothelialize and Remodel Basement Membranes. Organogenesis, vol. 8(2), 2012, 49-55.
Roy et al., Biomechanical Properties of Decellularized Porcine Common Carotid Arteries. Am. J. Physiol. Heart Circ. Physiol., vol. 289, (2005), H1567-H1576.
Saito, Development of bioartificial kidneys. Nephrology (Carlton). Oct. 2003. 8 Suppl:S10-5, (2003), 1.
Salizzoni, M., et al., Piggyback techniques versus classical technique in orthotopic liver transplantation: a review of 75 cases. Transplant Proc, 1994. 26(6): p. 3552-3.
Sarraf et al., Cell Proliferation Rates in an Artificial Tissue-Engineered Environment. Cell Prolif. Aug. 2005; vol. 38(4), p. 215-21.
Sayk et al., Histopathologic Findings in a Novel Decellularized Pulmonary Homograft: An Autopsy Study. Ann. Thorac. Surg, vol. 79(5), (2005), 1755-1758.
Schaner et al., Decellularized Vein as a Potential Scaffold for Vascular Tissue Engineering. J Vase Surg., vol. 40(1), ( 2004), 146-53.
Schenke-Layland et al. Complete Dynamic Repopulation of Decellularized Heart Valves by Application of Defined Physical Signals—an in Vitro Study. Cardiovasc. Res., vol. 60(3), (2003), 497-509.
Schenke-Layland et al. Impact of decellularization of xenogeneic tissue on extracellular matrix integrity for tissue engineering of heart valves. J. Struct. Biol., 143, (2003), 201-208.
Schlager, Gunther, Kidney Weight in Mice: Strain Differences and Genetic Determination. The Journal of Heredity, 59, (1968), 171-174.
Schmidt et al., Acellular Vascular Tissues: Natural Biomaterials for Tissue Repair and Tissue Engineering. Biomaterials, vol. 21(22), (2000), 2215-2231.
Seaberg, et al. Stem and progenitor cells: the premature desertion of rigorodefinitions. Trends Neurosci. Mar. 2003;26(3), p. 125-31.
Sekine et al. Cardiomyocyte Bridging Between Hearts and Bioengineered Myocardial Tissues with Mesenchymal Transition of Mesothelial Cells. J. Heart Lung Transplant 25, (2006), 324-332.
Shimizu et al., Fabrication of Pulsatile Cardiac Tissue Grafts using a Novel 3-Dimensional Cell Sheet Manipulation Technique and Temperature-Responsive Cell Culture Surfaces. Circ Res., vol. 90(3), (2002).
Shirakigawa, et al., Base structure consisting of an endothelialized vascular-tree network and hepatocytes for whole liver engineering. J Biosci Bioeng, 2013. 116(6): p. 740-5.
Shyy et al., Role of Integrins in Endothelial Mechanosensing of Shear Stress. Circ. Res., vol. 91, (2002), 769-775.
Song et al., Enhanced In Vivo Function of Bioartificial Lungs in Rats. Ann. Thorac. Surg., vol. 92(3), (2011), 998-1006.
Song, et al., Organ engineering based on decellularized matrix scaffolds. Trends Mol Med. Aug. 2011; vol. 17(8):424-32.
Song, J. J. et al., Regeneration and Experimental Orthotopic Transplantation of a Bioengineered Kidney. Nature Medicine, vol. 19, 646-651 (2013).
Soto-Gutierrez et al. A Whole-Organ Regenerative Medicine Approach for Liver Replacement. Tissue Engineering Part C: Methods, 17(6), (2011), 677-686.
Stem Cell Definition. Printout from http://www.google.com/search? Pulled Oct. 1, 2021.
Stevenson et al., Left Ventricular Assist Device as Destination for Patients Undergoing Intravenous Inotropic Therapy. A Subset Analysis from REMATCH (Randomized Evaluation of Mechanical Assistance in Treatment of Chronic Heart Failure. Circulation, vol. 110, (2004), 975-981.
STOCUM Regenerative biology and medicine. J. Musculoskelet Neuronal Interact. Mar. 2002;2(3), p. 270-3, (2002).
Suchy, F., T. Yamaguchi, and H. Nakauchi, iPSC-Derived Organs In Vivo: Challenges and Promise. Cell Stem Cell, 2018. 22(1): p. 21-24.
Sudo et al. Reconstruction of 3d stacked-up structures by rat small hepatocytes on microporous membranes. FASEB J., vol. 19, (2005), 1695-1697.
Sun et al., Development of a Closed Bioreactor System for Culture of Tissue-Engineered Skin at an Air-Liquid Interface. Tissue Engineering 11, (2005), 1824-1831.
Suresh et al., A Retrospective Study of the Prognostic Impact of Cytokine Secretion in Mixed Lymphocyte Culture on Long-Term Graft Function Following Allogeneic Renal Transplantation. Transpl Int. Sep. 2005; vol. 18(9): 1067-71.
Swanson et al. Characterization of Mitral Valve Anterior Leaflet Perfusion Patterns. NIH Public Access, published in final edited form as: J. Heart Valve Dis., vol. 18(5), (2009), 488-495.
Takagi et al. n Vivo Recellularization of Plain Decellularized Xenografts with Specific Cell Characterization in the Systemic Circulation: Histological and Immunohistochemical Study. Artificial Organs 30(4), (2006), 233-241.
Tanaka, Masatake et al., The Hepatic Lymphatic Vascular System: Structure, Function, Markers, and Lymphangiogenesis, Cell Mol Gastroenterol Hepatol. Nov. 2016; 2(6): 733-749.
Taylor et al. Regenerating Functional Myocardium: Improved Performance after Skeletal Myoblast Transplantation. Nature Medicine, vol. 4(8), (1998), p. 929-933.
Teebken et al. Tissue engineering: in vitro creation of tissue substitutes. Zentralblatt fur Chirurgie 132.3 (2007), p. 236-246.
Teebken et al., Tissue Engineering of Vascular Grafts: Human Cell Seeding of Decellularised Porcine Matrix. European J. Vase. Endovasc. Surgery, vol. 19, (2000), 381-386.
Toni et al., The Bioartificial Thyroid: a Biotechnical Perspective in Endocrine Organ Engineering for Transplantation Replacement. Acta Biomed, vol. 78 Suppl , (2007), 129-155.

(56) References Cited

OTHER PUBLICATIONS

Tower et al., Fiber alignment imaging during mechanical testing of soft tissues, Ann Biomed Eng., 2002, vol. 30, No. 10, p. 1221-33.
Uchimura et al. Novel method of preparing acellular cardiovascular grafts by decellularization with poly(ethylene glycol). J. Biomed. Mater. Res. 67A, (2003), 834-837.
Uygun et al. Decellularization and recellularization of whole livers. Journal of visualized experiments: JoVE, vol. 48 (2011).
Uygun, B.E., et al., Application of Whole-Organ Tissue Engineering in Hepatology. Nat Rev Gastroenterol Hepatol, 2012, vol. 9, No. 12, p. 738-744.
Uygun, Basak E, et al., Organ Reengineering Through Development of a Transplantable Recellularized Liver Graft using Decellularized Liver Matrix, Nature Medicine, vol. 16, No. 7, (2010), 814-820.
Uzarski, U.S., et al., Dual-Purpose Bioreactors to Monitor Noninvasive Physical and Biochemical Markers of Kidney and Liver Scaffold Recellularization. Tissue Engineering. Part C, Methods, 2015. 21(10): p. 1032-1043.
Van Putte, Bart P et al., Single-Pass Isolated Lung Perfusion Versus Recirculating Isolated Lung Perfusion with Melphalan in a Rat Model, Oct. 2002, The Annals of Thoracic Surgery 74(3):893-8.
Wagner, Susanne et al., The isolated Normothermic Hemoperfused Porcine Forelimb as a Test System for Transdermal Absorption Studies, Journal of Artificial Organs : The Official Journal of the Japanese Society for Artificial Organs. 6. 183-91, (2003).
Wang et al., Decellularized Liver Scaffolds Effectively Support the Proliferation and Differentiation of Mouse Fetal Hepatic Progenitors. J. Biomed Mater Res Part A, vol. 102A, (2014), 1025-1027.
Wang, B., et al., Functional Maturation of Induced Pluripotent Stem Cell Hepatocytes in Extracellular Matrix—A Comparative Analysis of Bioartificial Liver Microenvironments. Stem Cells Translational Medicine, 2016. 5(9): p. 1257-1267.
Wang, X., et al., 3D Bioprinting Technologies for Hard Tissue and Organ Engineering. Materials, 2016. 9(10):802.
Wang, Y., et al., Recent Advances in Decellularization and Recellularization for Tissue-Engineered Liver Grafts. Cells Tissues Organs, 2017. 204(3-4): p. 125-136.
Wang, Yunfang, et al., Lineage Restriction of Human Hepatic Stem Cells to Mature Fates Is Made Efficient by Tissue-Specific Biomatrix Scaffolds. Hepatology, vol. 53, (2011), 293-305.
Woods et al. Effectiveness of three extraction techniques in the development of a decellularized bone-anterior cruciate ligament-bone graft. Biomaterials, Elsevier Science Publishers, vol. 26, No. 35, (Dec. 1, 2005), 7339-7349.
Wrba, Heinrich, et al., The Action of Serum from Partially Hepatectomized Rats on Explants of Liver and Tumors. Cancer Research, (Jan. 1963): 1116-1120.
Written Opinion of the International Searching Authority dated Aug. 28, 2019 for International Application Serial No. PCT/US19/35449 (8 pages).
Xing et al., Hepatectomised patient sera promote hepatocyte differentiation of human-induced pluripotent stem cells, Digestive and Liver Disease, vol. 46, No. 8, 2014, p. 731-737.
Yagi et al. Human-Scale Whole-Organ Bioengineering for Liver Transplantation: A Regenerative Medicine Approach. Cell. Transplant., vol. 22(2), (2013), 231-242.
Yang et al., In Vitro Trans-Differentiation of Adult Hepatic Stem Cells into Pancreatic Endocrine Hormone-Producing Cells. Proc. Natl. Acad. Sci. USA, vol. 99(12), (2002), 8078-8083.
Zandonella, Tissue Engineering: The Beat Goes On. Nature, vol. 421, (2003), 884-886.
Zeltinger et al., Development and Characterization of Tissue-Engineered Aortic Valves. Tissue Engineering, vol. 7, (2001), 9-22.
Zhou et al., Effects of hepatectomized rat serum on the transdifferentiation of adult rat bone marrow cells into hepatocyte-like cells, Zhonghua Gan Zang Bing Za Zni, 2004, vol. 12, p. 730-733.
Zimmermann et al., Engineered heart tissue for regeneration of diseased hearts. Biomaterials, vol. 25(9), (2004), 1639-47.
Zimmermann et al., Engineered Heart Tissue Grafts Improve Systolic and Diastolic Function in Infarcted Rat Hearts. Nature Medicine, vol. 12(4), (2006), 452-458.
Seetapun et al., Eliminating the organ transplant waiting list: The future with perfusion decellularized organs, Surgery, 2017, vol. 161, p. 1474-1478.

USE OF RESECTED LIVER SERUM FOR WHOLE LIVER-ENGINEERING

CROSS-REFERENCE TO RELATED APPLICATIONS

This application is a continuation of U.S. application Ser. No. 15/697,078, filed Sep. 6, 2017, and claims the benefit of the filing date of U.S. Application No. 62/383,772, filed on Sep. 6, 2016, the disclosure of which is incorporated by reference herein

BACKGROUND

The liver is the one organ that can rapidly regenerate itself in vivo under certain conditions. One such condition is a partial liver resection or hepatectomy. Following a partial hepatectomy, the host liver quickly regenerates in a healthy mammal. While the liver is capable of regenerating itself under these conditions, which involves the proliferation of all liver-specific cells, in vitro hepatocytes demonstrate little or no proliferation and may quickly lose their functionality, e.g., as measured by albumin expression. The lack of in vitro proliferation and sustained functionality poses a challenge as the number of available hepatocytes for medical therapy is limited and the need continues to grow.

SUMMARY

The disclosure provides compositions and ex vivo methods of using blood or fractions thereof, e.g., serum, obtained from mammals such as a swine, ovine, caprine, bovine, equine, canine, feline, or human, subjected to liver surgery, for example, obtained following a partial hepatectomy, to increase the engraftment, proliferation and/or functionality of cells, e.g., hepatocytes, stem cells or stem cell-derived hepatocytes, seeded onto decellularlized liver or collagen grafts (e.g., scaffolds or substrates). In one embodiment, the scaffolds can include but are not limited to perfusion decellularized extracellular matrix constructs such as a perfusion decellularized whole liver, a perfusion decellularized liver lobe or a portion of, or a collagen sponge. In one embodiment, the blood is obtained following a recent hepatectomy, e.g., from about 2 hours to about 120 hours, for instance, from about 12 to about 96 hours, after the hepatectomy, and an amount of the blood or a fraction thereof is used to increase the seeding efficiency, proliferation, and/or functionality of cells including hepatocytes seeded onto various scaffolds ex vivo.

In one embodiment, a method to enhance engraftment, proliferation and/or function of cells seeded onto substrates is provided. The method includes providing a substrate comprising a decellularized extracellular matrix of a liver, a liver lobe or a portion thereof, or isolated collagen, and a population of cells comprising hepatocytes, endothelial cells or stem cells capable of differentiating into those cells, or any combination thereof. The substrate, the population of cells and an amount of an aqueous composition comprising isolated blood or a fraction thereof from a mammal subjected to liver resection, are contacted so as to enhance the engraftment, proliferation and/or function of the cells on or in the substrate. In one embodiment, the aqueous composition is prepared by collecting blood from a mammal subjected to a liver resection, and isolating serum from the blood. In one embodiment, the decellularized extracellular matrix is a human or porcine decellularized extracellular matrix of a liver. In one embodiment, the cells are iPS cells. In one embodiment, the cells are human embryonic stem cells. In one embodiment, the function of the cells is enhanced by about 5% to about 25%, about 5% to about 15%, about 10% to about 30%, about 10% to about 100% or about 200% to about 1000% in the presence of the composition relative to cells in the presence of the substrate but in the absence of the composition. In one embodiment, albumin expression is enhanced by about 10% to about 1000%. In one embodiment, the hepatocytes or endothelial cells are obtained from iPS cells. In one embodiment, the decellularized extracellular matrix of the liver contains an intact vascular network. In one embodiment, the substrate is contacted, e.g., perfused, with media before the cells are contacted with the substrate. In one embodiment, the substrate is contacted, e.g., perfused, with media after the cells are contacted with the substrate. In one embodiment, the substrate is perfused with media before or after the composition is contacted with the substrate. In one embodiment, the substrate that is contacted with cells is contacted with the composition comprising isolated blood or a fraction thereof, e.g., the composition comprises media and the isolated blood or isolated serum. In one embodiment, the composition is contacted with the cells for at least 12 hours up to at least 28 days, e.g., from 12 hours up to 10 to 12 days. In one embodiment, the media further comprises one or more exogenously added activators or inhibitors of differentiation pathways selected to provide for, in one embodiment, liver-specific differentiation. In one embodiment, the media further comprises one or more exogenously added activators or inhibitors of differentiation pathways selected to provide for, in one embodiment, endothelial cell-specific differentiation. In one embodiment, the population of cells is contacted with the substrate either by injection or perfusion, or a combination thereof. In one embodiment, the cells contacted with the composition express albumin, express HepParl, and/or deposit glycogen, or release albumin and urea, or any combination thereof. In one embodiment, the population comprises a plurality of different cell types. In one embodiment, the cells and the biological source of the substrate are allogeneic. In one embodiment, the cells and the biological source of the substrate are xenogeneic. In one embodiment, the cells are human hepatocytes and the substrate is from a non-human mammal. In one embodiment, the blood is allogeneic to the substrate or cells. In one embodiment, the blood is xenogeneic to the substrate or cells. In one embodiment, the collagen substrate is Collarx®, Collatamp® G, Collatamp® Eg, Sulmycin® Implant, Garamycin® Schwamm, Duracol®, Gentacol®, Garacol®, and Cronocol® or a collagen hydrogel gel processed by cross-linking of collagen with chemicals like poly epoxy compounds, carbodiimides, polyphenolic compounds, aldehydes, or acyl azide compounds.

Also provided is a composition useful to increase the engraftment, proliferation and/or functionality of cells prepared by collecting blood from a mammal subjected to a liver surgery such as liver resection, e.g., within about 96 to 120 hours of the resection, obtaining serum from the collected blood, and combining an amount of the serum or a portion thereof with tissue culture media.

In one embodiment, a composition comprises serum from a mammal subjected to a partial liver resection and tissue culture media. In one embodiment, the serum is collected within 96 to 120 hours of the resection. In one embodiment, the composition increases the ex vivo engraftment, proliferation and/or functionality of cells on a substrate.

DETAILED DESCRIPTION

Figure 1A:
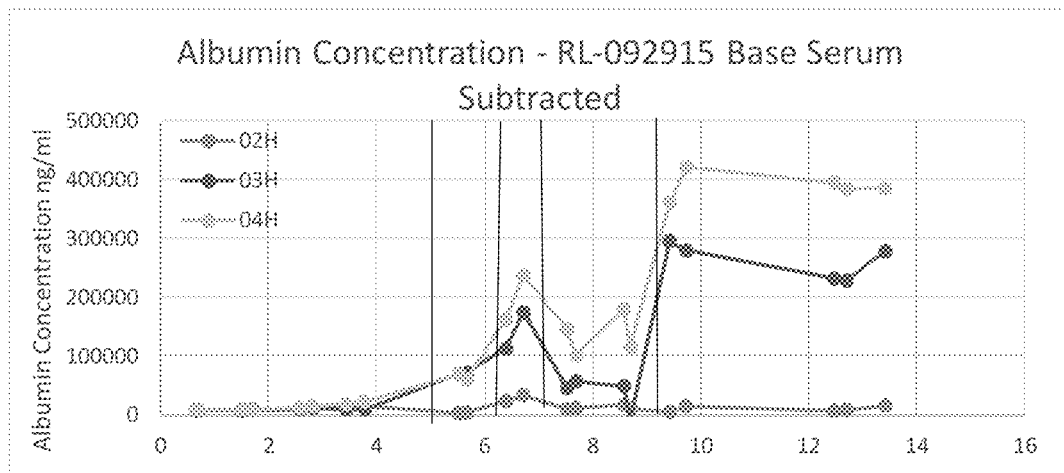
FIG. 1A. Graph of albumin concentration over time (base serum subtracted).
Figure 1B:
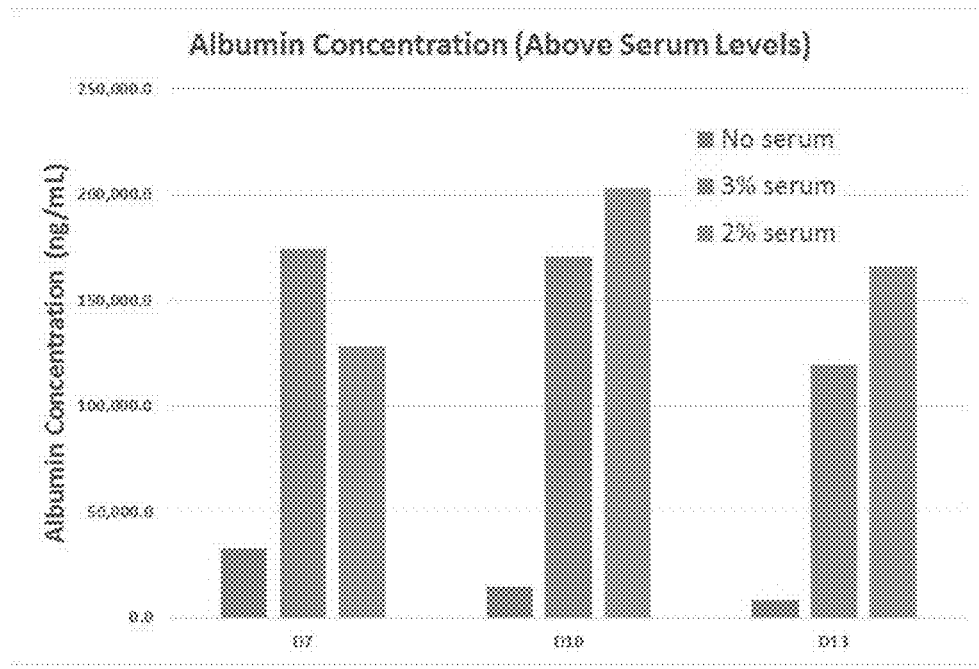
FIG. 1B. Graph of albumin concentration above serum levels in three animals.

To overcome the poor proliferation of hepatocytes in vitro, a blood fraction, e.g., serum or plasma, is isolated from a mammal following a partial hepatectomy and added to a three dimensional substrate having cells, such as hepatocytes in an amount that induces the engraftment, proliferation and/or increases the functionality of hepatocytes or induces the engraftment, proliferation, differentiation and/or function of stem cells in vitro. As described herein, when hepatectomy serum is added to a culture, an increase in cellular proliferation and albumin expression was obtained. More notable, when the serum was added to a perfusable liver system, such as a whole or partial perfusion decellularized liver substrate, the expression of albumin increased about 200% to about 1000% compared to controls (no serum).

The resulting systems are useful to expand human hepatocytes in a 3D cell culture system, e.g., as a source for ADME-Tox testing or cellular therapy. For example, the use of serum or plasma, or a plurality of molecules isolated therefrom, allows seeding of lower numbers of human hepatocytes, optionally in conjunction with endothelial and bile duct cells, in a substrate, and those cells can proliferate and grow in a liver construct ex vivo and optionally be employed for in vivo cell therapeutic uses, such as a bioengineered liver. The systems provide for increased functionality of seeded cells, including liver-specific cells, such as those derived from stem cells, and provide for increased functional differentiation of stem cells to hepatocytes or endothelial cells, or both, when the stem cells are seeded in or to a substrate, e.g., a perfusion decellularized liver or a portion thereof, following culture with the serum or plasma obtained following a hepatectomy.

The present disclosure provides for substrates seeded with cells including decellularized extracellular matrices (ECMs) that, through physical as well as molecular interactions, direct control of seeded cell behavior by controlling the environment of those cells. In one embodiment, the present disclosure provides decellularized livers or portions thereof or collagen seeded substrates having a population of cells, including combinations of different cell types, which seeded substrates are subjected to culture conditions, e.g., including perfusion of the blood or isolated fraction thereof, and optionally one or more soluble mediators, e.g., one or more of hepatocyte growth factor (HGF), VEGF, EGF, FGF, PDGF, or heparin, in combination with the blood or isolated fraction or prior to or subsequent to addition of the blood or fraction thereof, to enhance cell viability, engraftment, proliferation, differentiation, and/or functionality or including incubation (static) with the blood or isolated fraction thereof and optionally one or more of the soluble mediators in combination with the blood or isolated fraction or prior to or subsequent to addition of the blood or fraction thereof, which ECM structure, culture conditions and reagents, and optionally soluble mediator(s), result in viable functional cells. In particular, the invention provides for improved cell differentiation, growth, and phenotypic expression of improved growth and phenotypic expression of stem cells, both adult and embryonic, and improved growth and phenotypic expression of differentiated cells. In one embodiment, the system provides for the engraftment, growth (proliferation) and/or functional maintenance of primary cells or fetal derived cells, e.g., organ-specific cells obtained from fetal cells or neonate cells, and/or engraftment, proliferation, differentiation and/or function of stem cells. The use of the systems of the invention result in an increased percentage of functional differentiated liver cells, as well as endothelial cells. In one embodiment, the differentiated cells of the invention have at least 20% of the function of corresponding normal cells in vivo.

In particular, the substrates including perfusion decellularized ECMs are suitable for 3D culture of primary and stem cells in vitro, and for organ formation, as the substrate provides appropriate biological cues. The resulting bioreactor may be employed, for instance, to provide for stem cell expansion with control of differentiation, and xenografts that can be readily recovered from the cellularized constructs after expansion, differentiation, and/or matrix remodeling have occurred, or provided for organs, e.g., vascularized structures of organs, or tissues that contain functional cell populations that can be used for toxicology testing.

Perfusion Decellularized ECM

Studies have shown that connective tissue cells behave very differently in 3D as opposed to 2D cultures (Cukierman et al., Science, 294:1708 (2001)). For example, culture of fibroblasts on flat substrates induces a polarity that does not occur in vivo. Further, when fibroblasts and other cell types are cultured in 3D tissue-derived matrices, they develop mature integrin-containing focal adhesion complexes within minutes that resemble the complexes found in vivo, whereas only primitive adhesion complexes develop in 2D cultures or even simple 3D type I collagen gels or Matrigel. These adhesion complexes are required for appropriate growth factor-activated receptor signaling and rapid (within 5 minutes) initiation of synthesis of their own ECM components and factors that alter the ECM (Cukierman et al., 2001; Abbott, Nature, 424:870 (2003)). In addition, cells in ECM culture deposit autocrine growth factors into tissue-derived matrices, a process that may be required for appropriate presentation of the growth factor to target cells. Such factors are mainly secreted into the culture medium in 2D cultures.

As mentioned above, physical interactions with the ECM, in addition to chemical, molecular (e.g., soluble mediators), or genetic (cell-type) factors, may regulate cell fate. For example, ECM-based control of the cell may occur through multiple physical mechanisms, such as ECM geometry at the micro- and nanoscale, ECM elasticity, or mechanical signals transmitted from the ECM to the cells.

In one embodiment, the invention includes the use of perfusion decellularized ECMs that allow for better control of cell behavior, e.g., from adult or stem cells, through physical as well as molecular interactions. The perfusion decellularized matrices of the invention mimic the intricate and highly ordered nature of native ECM and the likely reciprocal interaction between cells and the ECM. In particular, the ECM may provide tissue-specific cues to stem cells. In particular, distinct matrix proteins may be important for the specificity of ECM via their contribution to the architecture of the ECM or via their ability to interact with growth factors and/or the resident cells themselves.

Perfusion decellularization of organ ECM provides an intact ECM that has the ability to provide the structural, biochemical, and mechanical properties to enable functional cell differentiation and maintenance. Thus, perfusion decellularization of organs allows organs to serve as a tissue/organ specific bioreactor for stem cell differentiation. Moreover, perfusion decellularization of organ ECM is superior to immersion in terms of preserving an intact matrix with structural and biochemical cues, including intact vasculature. In addition, perfusion decellularization provides advantages relative to immersion decellularization when tissue or organ thickness exceeds about 2 mm in thickness Decellularization of Organs Decellularization generally includes the following steps: stabilization of the solid organ, e.g., a vascularized structure thereof, decellularization of the solid organ, renaturation and/or neutralization of the solid organ, washing the solid organ, degradation of any DNA remaining on the organ, disinfection of the organ or tissue and homeostasis of the organ.

The initial step in decellularizing an organ vascularized structure is to cannulate the organ. The vessels, ducts, and/or cavities of an organ may be cannulated using methods and materials known in the art. Next, the cannulated organ vascularized structure is perfused with a cellular disruption medium. Perfusion through an organ can be multi-directional (e.g., antegrade and retrograde).

Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988.

Briefly, for Langendorff perfusion, the aorta is cannulated and attached to a reservoir containing physiological solution to allow the heart to function outside of the body for a specified duration of time. To achieve perfusion decellularization the protocol has been modified to perfuse a cellular disruption medium delivered in a retrograde direction down the aorta either at a constant flow rate delivered, for example, by an infusion or roller pump or by a constant hydrostatic pressure pump. In both instances, the aortic valves are forced shut and the perfusion fluid is directed into the coronary ostia (thereby perfusing, via antegrade, the entire ventricular mass of the heart), which then drains into the right atrium via the coronary sinus. For working mode perfusion, a second cannula is connected to the left atrium and perfusion can be changed to retrograde.

In one embodiment, a physiological solution includes phosphate buffer saline (PBS). In one embodiment, the physiological solution is a physiologically compatible buffer supplemented with, e.g., nutritional supplements (for instance, glucose). For liver, the physiological solution may be Krebs-Henseleit buffer having 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$) supplemented with 2% BSA.

Methods are known in the art for perfusing other organs.

One or more cellular disruption media may be used to decellularize an organ. A cellular disruption medium generally includes at least one detergent such as but not limited to SDS, PEG, CHAPS or Triton X. A cellular disruption medium can include water such that the medium is osmotically incompatible with the cells. Alternatively, a cellular disruption medium can include a buffer (e.g., PBS) for osmotic compatibility with the cells. Cellular disruption media also may include enzymes such as, without limitation, one or more collagenases, one or more dispases, one or more DNases, or a protease such as trypsin. In some instances, cellular disruption media also or alternatively may include inhibitors of one or more enzymes (e.g., protease inhibitors, nuclease inhibitors, and/or collegenase inhibitors).

In certain embodiments, a cannulated organ may be perfused sequentially with two different cellular disruption media. For example, the first cellular disruption medium may include an anionic detergent such as SDS and the second cellular disruption medium can include an ionic detergent such as Triton X. Following perfusion with at least one cellular disruption medium, a cannulated organ or tissue may be perfused, for example, with wash solutions and/or solutions containing one or more enzymes such as those disclosed herein. Alternating the direction of perfusion (e.g., antegrade and retrograde) may assist in decellularizing the entire organ or tissue. Decellularization generally decellularizes the organ from the inside out, resulting in very little damage to the ECM. An organ or tissue may be decellularized at a suitable temperature between 4 and 40° C. Depending upon the size and weight of an organ or tissue and the particular detergent(s) and concentration of detergent(s) in the cellular disruption medium, an organ or tissue generally is perfused from about 0.05 hours to about 5 hours, per gram of solid organ or tissue (generally >50 grams), or about 2 hours to about 12 hours, per gram of solid organ or tissue for organs (generally <50 grams), with cellular disruption medium. Including washes, an organ may be perfused for up to about 0.75 hours to about 10 hours per gram of solid organ or tissue (generally >50 grams), or about 12 hours to about 72 hours, per gram of tissue (generally <50 grams). Decellularization time is dependent upon the vascular and cellular density of the organ or tissue with limited scaling for overall mass. Therefore, as general guidance the time ranges and masses above are provided. Perfusion generally is adjusted to physiologic conditions including pulsatile flow, rate and pressure.

A decellularized organ has the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures or removal of over 97% of detectable DNA as measured by fluorometric assay. Residual cell debris may be removed from the decellularized organ or tissue.

The morphology and the architecture of the ECM is maintained during and following the process of decellularization. "Morphology" as used herein refers to the overall shape of the organ, tissue or of the ECM, while "architecture" as used herein refers to the exterior surface, the interior surface, and the ECM therebetween.

The morphology and architecture of the ECM may be examined visually and/or histologically. For example, the basal lamina on the exterior surface of a solid organ or within the vasculature of an organ or tissue should not be removed or significantly damaged due to perfusion decellularization. In addition, the fibrils of the ECM should be similar to or significantly unchanged from that of an organ or tissue that has not been decellularized.

One or more compounds may be applied in or on a decellularized organ, for example, preserve the decellularized organ, or to prepare the decellularized organ for recellularization and/or to assist or stimulate cells during the recellularization process. Such compounds include, but are not limited to, one or more growth factors (e.g., VEGF, DKK-1, FGF, PDGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ may be further treated with, for example, irradiation (e.g., UV, gamma) to reduce or eliminate the presence of any type of microorganism remaining on or in a decellularized organ or tissue.

Exemplary Perfusion Decellularization

PEG Decellularization Protocol

Livers are washed in 200 ml PBS containing 100 U/mL penicillin, 0.1 mg/mL Streptomycin, 0.25 µg/mL Amphotericin B, 1000 U of hepatin, and 2 mg of Adenocard with no recirculation. Livers are then decellularized with 35 ml polyethyleneglycol (PEG; 1 g/mL) for up to 30 minutes with manual recirculation. The organ is then washed with 500 mL PBS for up to 24 hours using a pump for recirculation. The washing step is repeated at least twice for at least 24 hours each time. Livers are exposed to 35 ml DNase I (70 U/mL) for at least 1 hour with manual recirculation. The organs are washed again with 500 ml PBS for at least 24 hours.

Triton X and Trypsin Decellularization Protocol

Livers are washed in 200 ml PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. Livers are then decellularized with 0.05% Trypsin for 30 minutes followed by perfusion with 500 mL PBS containing 5% Triton-X and 0.1% ammonium-hydroxide for about 6 hours. Livers are perfused with deionized water for about 1 hour, and then perfused with PBS for 12 hours. Livers are then washed 3 times for 24 hours each time in 500 mL PBS using a pump for recirculation. The livers are perfused with 35 ml DNase I (70 U/mL) for 1 hour with manual recirculation and washed twice in 500 mL PBS for at least about 24 hours each time using a pump for recirculation.

1% SDS Decellularization Protocol

Livers are washed in 200 mL PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. The livers are decellularized with 500 mL water containing 1% SDS for at least about 6 hours using a pump for recirculation. The livers are then washed with deionized water for about 1 hour and washed with PBS for about 12 hours. The livers are washed three times with 500 mL PBS for at least about 24 hours each time using a pump for recirculation. The liver is then perfused with 35 ml DNase I (70 U/mL) for about 1 hour using manual recirculation, and washed three times with 500 mL PBS for at least about 24 hours each time using a pump for recirculation.

Triton X Decellularization Protocol

Livers are washed with 200 mL PBS containing 100 U/mL Penicillin, 0.1 mg/ml Streptomycin, 0.25 µg/mL Amphotericin B, 1000 U of hepatin, and 2 mg of Adenocard (adenosine) for at least about 20 minutes with no recirculation. Livers are then decellularized with 500 mL water containing 5% Triton X and 0.1% ammonium hydroxide for at least 6 hours using a pump for recirculation. Livers are then perfused with deionized water for about 1 hour and then with PBS for about 12 hours. Livers are washed by perfusing with 500 mL PBS 3 times for at least 24 hours each time using a pump for recirculation. Livers are then perfused with 35 ml DNase I (70 U/mL) for about 1 hour using manual recirculation, and washed three times in 500 ml PBS for about 24 hours each time.

Livers may be perfused at a coronary perfusion pressure of 60 cm $H_2O$. Although not required, the livers may be mounted in a decellularization chamber and completely submerged and perfused with PBS containing antibiotics for 72 hours in recirculation mode at a continuous flow of 5 mL/minute to wash out as many cellular components and detergent as possible.

Detection of Liver Decellularization

Successful decellularization may be measured by the lack of myofilaments and nuclei in histologic sections. Successful preservation of vascular structures may be assessed by perfusion with 2% Evans Blue prior to embedding tissue sections. Highly efficient decellularization is observed when a liver is first perfused antegradely with an ionic detergent (1% sodium-dodecyl-sulfate (SDS), approximately 0.03 M) dissolved in deionized $H_2O$ at a constant coronary perfusion pressure and then perfused antegradely with a non-ionic detergent (1% Triton X-100) to remove the SDS and presumably to renature the extracellular matrix (ECM) proteins. Intermittently, the liver may be perfused retrogradely with phosphate buffered solution to clear obstructed capillaries and small vessels.

To demonstrate intact vascular structures following decellularization, a decellularized liver may be stained via Langendorff perfusion with Evans Blue to stain vascular basement membrane and quantify macro- and micro-vascular density. Further, polystyrene particles may be perfused into and through a liver to quantify coronary volume, the level of vessel leakage, and to assess the distribution of perfusion by analyzing coronary effluent and tissue sections. A combination of three criteria are assessed and compared to isolated non-decellularized liver: 1) an even distribution of polystyrene particles, 2) significant change in leakiness at some level 3) microvascular density.

Exemplary Perfusion Decellularization of Liver

For liver isolation, the caval vein is exposed through a median laparotomy, dissected and cannulated using a mouse aortic cannula (Radnoti Glass, Monrovia, Calif.). The hepatic artery and vein and the bile duct are transected and the liver was carefully removed from the abdomen and submerged in sterile PBS (Hyclone, Logan, Utah) to minimize pulling force on portal vein. 15 minutes of heparinized PBS perfusion is followed by 2-12 hours of perfusion with 1% SDS (Invitrogen, Carlsbad, Calif.) in deionized water and 15 minutes of 1% Triton-X (Sigma, St. Louis, Mo.) in deionized water. The liver is then continuously perfused with antibiotic containing PBS (100 U/ml penicillin-G (Gibco, Carlsbad, Calif.), 100 U/ml streptomycin (Gibco, Carlsbad, Calif.), 0.25 µg/ml Amphotericin B (Sigma, St. Louis, Mo.)) for 124 hours.

120 minutes of SDS perfusion followed by perfusion with Triton-X 100 are sufficient to generate a completely decellularized liver. Movat pentachrome staining of decellularized liver confirms retention of characteristic hepatic organization with central vein and portal space containing hepatic artery, bile duct and portal vein.

Recellularization of Organs

A decellularized organ or portion thereof is contacted with a population of cells, either differentiated (mature or primary) cells or stem cells. Thus, the cells can be committed, single-lineage cells. The cells may be undifferentiated cells, partially differentiated cells, or fully differentiated cells including fetal derived cells. Cells may include precursor or "adult" derived stem cells. Cells useful in the matrices of the invention include embryonic stem cells (as defined by the National Institute of Health (NIH); see, for example, the Glossary at stemcells.nih.gov on the World Wide Web) and iPS cells.

Examples of cells that can be used to recellularize an organ or portion thereof include, without limitation, embryonic stem cells, umbilical cord blood cells, tissue-derived stem or progenitor cells, bone marrow-derived step or progenitor cells, blood-derived stem or progenitor cells, mesenchymal stem cells (MSC), multipotent adult progenitor cells (MAPC), or iPS cells Additional cells that can be used include microvasculature endothelial cells, aortic endothelial cells, coronary endothelial cells, microvascular endothelial cells, venous endothelial cells, arterial endothelial cells, and hepatocytes. Bone marrow-derived stem cells such as bone marrow mononuclear cells (BM-MNC), endothelial or vascular stem or progenitor cells, and peripheral blood-derived stem cells such as endothelial progenitor cells (EPC) may also be used as cells.

The number of cells that are introduced into and onto a perfusion decellularized scaffold may depend both the size and weight of the organ or portion thereof and the type of cells. Different types of cells may have different tendencies as to the population density those cells will reach. By way of example, a decellularized organ or tissue can be "seeded" with at least about 1,000 (e.g., at least 10,000, 100,000, 1,000,000, 10,000,000, or 100,000,000) cells; or can have from about 1,000 cells/mg tissue (wet weight, e.g., prior to decellularization) to about 10,000,000 cells/mg tissue (wet weight) attached thereto.

Cells can be introduced ("seeded") into a decellularized organ by injection into one or more locations. In addition, more than one type of cell may be introduced into a decellularized organ or portion thereof. For example, a population of differentiated cell types can be injected at multiple positions in a decellularized organ or tissue or different cell types may be injected into different portions of a decellularized organ or tissue. Alternatively, or in addition to injection, cells or a cocktail of cells may be introduced by perfusion into a cannulated decellularized organ or portion thereof. For example, cells can be perfused into a decellularized organ using a perfusion medium, which can then be changed to an expansion and/or differentiation medium to induce growth and/or differentiation of the cells. Location specific differentiation may be achieved by placing cells into the various locations.

During recellularization, an organ or portion thereof is maintained under conditions in which at least some of the cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or portion thereof and the regenerative cells attached thereto are maintained in a suitable environment. For example, the cells may require a nutritional supplement (e.g., nutrients and/or a carbon source such as glucose), exogenous hormones or growth factors, and/or a particular pH.

Cells may be allogeneic to a decellularized organ or portion thereof (e.g., a human decellularized organ or portion thereof seeded with human cells), or cells may be xenogeneic to a decellularized organ or portion thereof (e.g., a pig decellularized organ or tissue seeded with human cells). "Allogeneic" as used herein refers to cells obtained from the same species as that from which the organ or portion thereof originated (e.g., related or unrelated individuals), while "xenogeneic" as used herein refers to cells obtained from a species different than that from which the organ or portion thereof originated.

Stem or progenitor media may contain a variety of components including, for example, KODMEM medium (Knockout Dulbecco's Modified Eagle's Medium), DMEM, Ham's F12 medium, Williams E Media, FBS (fetal bovine serum), FGF2 (fibroblast growth factor 2), KSR or hLIF (human leukemia inhibitory factor). The cell differentiation media may also contain supplements such as L-Glutamine, NEAA (non-essential amino acids), P/S (penicillin/streptomycin), N2, B27 and beta-mercaptoethanol. It is contemplated that additional factors may be added to the cell differentiationmedia, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In one embodiment, perfusion decellularized matrices are combined with iPS or ES cells differentiated using the embryoid body (EB) method. For example, human iPS cell lines reprogrammed by transduction, e.g., lentiviral-mediated transduction, of transcription factors (OCT4, SOX2, NANOG and LIN28; Oct3/4, Sox2, Klf4, and c-Myc; or Oct3/4, Sox2, and Klf4) are employed. iPS clones of fetal origin or of newborn origin may be employed. Human ES cell lines may also be employed. iPS cells and ES cells may be maintained on irradiated mouse embryonic fibroblasts (MEFs) at a density of 19,500 cells/cm$^2$ in 6-well culture plates (Nunc) in DMEM/F12 culture medium supplemented with 20% KnockOut serum replacer (Invitrogen), 0.1 mmol/L nonessential amino acids, 1 mmol/L L-glutamine, and 0.1 mmol/L β-mercaptoethanol (Sigma). In addition, the medium may be supplemented with 100 ng/mL, zebrafish basic fibroblast growth factor for iPS cells, and with 4 ng/mL human recombinant basic fibroblast growth factor (Invitrogen) for hES cells. iPS and ES cell lines may also be maintained on gelatinized 100-mm dishes in DMEM (Sigma-Aldrich) containing 15% fetal calf serum (FCS; Sigma-Aldrich), 0.1 μmol/L 2-mercaptoethanol (2ME), and 1,000 units/ml LIF (Chemicon International). For differentiation, these cells may treated with 0.25% Trypsin/ethylenediaminetetraacetic acid (GIBCO), and transferred to gelatinized 6-well plates in α-minimum essential medium (GIBCO) supplemented with 10% FCS and 0.05 μmol/L 2ME, at a concentration of 3×10$^4$ cells/well.

Colonies may be detached from culture plates by incubating with 1 mg/mL dispase (Gibco) solution at 37° C. for 8 to 15 minutes and placed in ultralow attachment plates in suspension culture, e.g., for 4 days. During suspension culture, the medium may be changed at day 1 followed by culture for another 3 days without medium change. EBs are then plated on 0.1% gelatin-coated culture plates, e.g., at the density or 50 to 100 EBs per well, or in the perfusion decellularized ECM and cultured in differentiation medium (e.g., changed daily).

In some instances, an organ or tissue generated by the methods described herein is to be transplanted into a patient. In those cases, the cells used to recellularize a decellularized organ or tissue can be obtained from the patient such that the cells are "autologous" to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue may be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

The progress of cells can be monitored during recellularization. For example, the number of cells on or in an organ or tissue can be evaluated by taking a biopsy at one or more time points during recellularization. In addition, the amount of differentiation that cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, Current Protocols in Immunology, 2005, Coligan et al., Eds., John Wiley & Sons, Chapters 3 and 11. Nucleic acid assays as well as morphological and/or histological evaluation can be used to monitor recellularization.

Exemplary Liver Cell Lineage Differentiation

Hepatocyte differentiation from various stem cell populations is either a multi-step procedure consisting of separate treatments with BMPs and FGFs to commit cells to the hepatic lineage followed by a maturation step which uses dexamethasone and IL6, or a single differentiation step using HGF and EGF. Both of these methods yield hepatocytes-like cells capable of expressing key hepatocyte markers including CXCR4, SOX17, FOXA2, albumin, phosphoenolpyruvate carboxykinase (PCK), glumatime synthetase (GS), and various P450 enzymes. To obtain functional hepatocytes, perfusable liver ECM scaffold is employed to support hepatocyte differentiation in a defined 3D culture environment. The perfused decellularized matrix allows for perfusion through intact vascular network whereas other decellularization technologies disrupt the vascular network and extracellular matrix thus not allowing for perfusion.

A hESC line, H9 (Madison, Wis., http://www.wicell.org) is cultured and maintained as described in protocols from the provider. Induction of hESC into definitive endoderm (DE) is initiated under conditions without serum in RPMI 1,640 medium (Invitrogen, Carlsbad, Calif., http://www.invitrogen.com) supplemented with 100 ng/mL of Activin A (R&D Systems Inc., Minneapolis, http://www.rndsystems.com), 2 mM L-glutamine, and 1% antibiotic-antimycotic for 48 hours. Then the same medium is supplemented with 1×B27 supplement (Invitrogen) and 0.5 mM sodium butyrate for another 3-6 days. The DE cells are then split with trypsin and reseeded at a ratio of 1:1-2 on collagen I-coated plates for hepatic differentiation with the culture medium, supplemented with FGF-4 (20 ng/mL), HGF (20 ng/mL), BMP2, and BMP4 (10 ng/mL each) (R & D Systems). The next day the medium is refreshed with the same medium plus 0.5% dimethyl sulfoxide (DMSO) for 10-14 days. As an alternative, the DE cells are differentiated directly, without splitting, using the same medium mentioned above. Then the cells are further differentiated and maintained in hepatocyte culture medium supplemented with SingleQuots (Lonza, Walkersville, Md., http://www.lonza.com), plus 2-5% fetal bovine serum (FBS), FGF-4 (20 ng/mL), HGF (20 ng/mL), Oncostatin M (50 ng/mL) (R & D Systems), 100 nM Dexamethasone, and 0.5% DMSO until use.

Cholangiocyte progenitors were derived from hiPSCs by first differentiation into Foregut Progenitor cells (FP) as described in Hanna et al., *Nat. Protocol.*, 8:430 (2013) and Hanna et al., *Stem Cell Reports*, 1:293 (2013). Bipotent hepatoblasts were generated by culturing FPs in RPMI (Gibco, Invitrogen)+B27 supplemented with SB-431542 (10 µM, Tocris Bioscience) and BMP4 (50 ng/mL) for 4 days. To induce biliary specification, hepatoblasts were cultured for another 4 days in the presence of RPMI (Gibco, Invitrogen)+B27 supplemented with FGF10 (50 ng/mL Peprotech), activin-A (50 ng/mL) and RA (3 µM, Sigma-Aldrich).

Human CPs were passaged using Cell Dissociation Buffer (Gibco, Life Technologies) and suspended at a density of $8 \times 10^4$ cells/mL, in a mixture of 40% matrigel (BD Biosciences, catalogue number: 356237) and 60% William's E medium (Gibco, Life Technologies) supplemented with 10 mM nicotinamide (Sigma-Aldrich), 17 mM sodium bicarbonate (Sigma Aldrich), 0.2 mM 2-Phospho-L-ascorbic acid trisodium salt (Sigma-Aldrich), 6.3 mM sodium pyruvate (Invitrogen), 14 mM glucose (Sigma-Aldrich), 20 mM HEPES (Invitrogen), ITS+ premix (BD Biosciences), 0.1 uM dexamethasone (R&D Systems), 2 mM Glutamax (Invitrogen), 100 U/mL penicillin per 100 µg/mL streptomycin and 20 ng/mL EGF (R&D Systems). A 50 µL droplet of the cell suspension was added in the centre of each well of a 24-well plate; the gel was allowed 1 hour at 37° C. to solidify and then overlaid with William's E medium with supplements. The medium was changed every 48 hours and the cells were cultured for a total of 10 days.

Using same methodology, CLC organoids have been cultured in multiple formats ranging from 6 to 96 well plates. To generate large numbers of CLC organoids, multiple 50 µL droplets were added in a well of a 6 well plate or a 10 cm dish. To provide a large number of wells compatible with high throughput screening and large scale experiments 30 µL droplets were added in a well of a 96 well plate. In both cases, the gel was allowed 1 hour at 37° C. to solidify and then overlaid with William's E medium with supplements.

For differentiation of hESC/hiPSC-derived hepatoblasts into cholangiocytes, at days 10-12 of differentiation, hESC/hiPSC-hepatoblasts were harvested with cell dissociation buffer (0.1 mg/mL EDTA, 0.5 mg/mL BSA in PBS) and seeded onto 12-well collagen I-coated plates (BD Biosciences) with plating medium (William's E/Ham F12 1:1, 10% FBS [PAA Laboratories], 1 mg/mL fraction V fatty acid-free BSA [Sigma], 1 mM L-glutamine) for 4 hours. Cells were then incubated overnight with biliary differentiation medium (BDM) (William's E/Ham F12 1:1, 10-5 M linoleic acid-Albumin [Sigma L9530], $5.10^{-8}$ M 3,3',5-Triiodo-L-thyronine [Sigma T2752], 0.2 IU Insulin, $6.10^{-4}$ M Vitamin C [Boyer], $6.10^{-4}$ M human apo-transferrin

[Sigma T5391], 1 mM sodium pyruvate [Gibco]). The next day, cells were incubated with BDM supplemented with 50 ng/mL human growth hormone (GH, Sigma H5916) and 25 ng/mL EGF for three days. Cells were then incubated with 10 ng/ml Interleukin 6 (IL-6, Miltenyi 130-093-929) for another three days. At day 17, cells were passaged on collagen I-coated 12-well plates as described for the first passage. At day 18, BDM medium was supplemented with 10 ng/mL IL-6 for three days. Finally, the cells were incubated in 10 μM sodium taurocholate hydrate (Sigma 86339) for 2 days. For the transcriptome analysis, μM Sodium Butyrate (NaBut, Sigma 303410) was added to the medium between days 21 to 23 (2 days).

For differentiation of HepaRG progenitors into cholangiocytes, HepaRG-HB were treated for 2 days with IL-6 (10 ng/mL), then for 2 days with sodium taurocholate hydrate (10 nM) and then for 2 days with sodium taurocholate hydrate (10 nM) and sodium butyrate (1.8 μM) to prevent spontaneous differentiation along the hepatocytic lineage.

The presence of a functional vascular bed conduit in a decellularized matrix, such as liver matrix, allows for control of stem cell engraftment and characterization of metabolic function in vitro. For example, cells are introduced via portal vein perfusion recirculation into liver matrix. Cells may be introduced one or more times, e.g., with 10 minute intervals between each infusion. Cell viability and distribution in the parenchyma may be determined. Engraftment efficiency is determined. In addition, the presence of bile ducts in the decellularized liver matrix, allows for the seeding and control of stem cells, liver progenitor, hepatoblast cells and the like, and engraftment and differentiation thereof into biliary cells including cholangiocytes. After seeding, the recellularized liver grafts may be transferred into a specially designed perfusion chamber for in vitro culture. The perfusion chamber has two hermetically sealed silicon sheets, forming a pouch filled with culture medium; this design avoids rigid surfaces, preventing development of pressure spots, while enabling sterile culture of the recellularized grafts up to 2 weeks in vitro.

The recellularized graft is continuously perfused. Cell viability is maintained during culture, and quantification of TUNEL-positive cells may be conducted, e.g., to determine cells that are apoptotic. The functional characteristics of engrafted cells in the decellularized matrix may be assessed via immunostaining of UDP glucuronosyltransferase 1 family, polypeptide A1 (Ugt1a), a sensitive enzyme with a short half-life (e.g., about 50 minutes) whose presence indicated hepatocyte viability and function, glucose-6-phosphatase, catalytic subunit (G6pc) and albumin. The level of immunostaining for these markers in engrafted hepatocytes is similar to that in normal livers.

Hepatocyte function may be assessed by immunocytochemical detection of CYP1A1 and CYP3A4 proteins, by the periodic acid Schiff (PAS) stain to prove glycogen synthesis and by expression of the hepatocyte markers phosphoenolpyruvate carboxykinase (PCK) and glutamine synthetase (GS) on the protein level using western blot analyses.

To assess the metabolic activity of engrafted hepatocytes, hepatocyte albumin production and urea synthesis may be quantified. Analysis of the expression of drug metabolism enzymes via quantitative RT-PCR may reveal expression levels of drug metabolism enzymes, e.g., Cyp2c11 (encoding cytochrome P450, subfamily 2, polypeptide 11) Gstm2 (glutathione S-transferase mu 2), Ugt1a1 (encoding UDP glucuronosyltransferase-1 family, polypeptide A1) and Cyp1a1 (encoding cytochrome P450, family-1, subfamily a, polypeptide 1) may be expressed in the recellularized liver at similar levels to those in normal liver. Adh1 (encoding alcohol dehydrogenase-1) and Cyp3a18 (encoding cytochrome P450, family 3, subfamily a, polypeptide 18) expression levels may also be determined.

Controlled System for Decellularizing and/or Recellularizing an Organ or Portion Thereof A system (e.g., a bioreactor) for decellularizing and/or recellularizing an organ or tissue generally includes at least one cannulation device for cannulating an organ or tissue, a perfusion apparatus for perfusing the organ or portion thereof through the cannula(s), and means (e.g., a containment system) to maintain a sterile environment for the organ or portion thereof. Cannulation and perfusion are well-known techniques in the art. A cannulation device generally includes size-appropriate hollow tubing for introducing into a vessel, duct, and/or cavity of an organ or tissue. Typically, one or more vessels, ducts, and/or cavities are cannulated in an organ. A perfusion apparatus can include a holding container for the liquid (e.g., a cellular disruption medium) and a mechanism for moving the liquid through the organ (e.g., a pump, air pressure, gravity) via the one or more cannulae. The sterility of an organ or portion thereof during decellularization and/or recellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize and recellularize organ or a portion thereof as described herein can possess the ability to monitor certain perfusion characteristics (e.g., pressure, volume, flow pattern, temperature, gases, pH). The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the system (e.g., bioreactor) and/or the organ or portion thereof. For example, sensors can be used to monitor the pressure of a liquid moving through a cannulated organ or portion thereof, the ambient temperature in the system and/or the temperature of the organ or tissue; the pH and/or the rate of flow of a liquid moving through the cannulated organ or portion thereof; and/or the biological activity of a recellularizing organ or tissue. In addition to having sensors for monitoring such features, a system for decellularizing and/or recellularizing an organ or portion thereof also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, and/or a compliance chamber. To help ensure stable conditions (e.g., temperature), the chambers, reservoirs and tubings can be water-jacketed.

A system for generating an organ or portion thereof may be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, may receive and process information from one or more of the sensors. Such a storage medium in conjunction with a programmable processor also can transmit information and instructions back to the bioreactor and/or the organ or tissue.

An organ or portion thereof undergoing recellularization may be monitored for biological activity. The biological activity can be that of the organ or portion thereof itself. In addition, the biological activity of the cells attached to the organ or tissue may be monitored, for example, for ion transport/exchange activity, cell division, and/or cell viability. See, for example, Laboratory Textbook of Anatomy and Physiology (2001, Wood, Prentice Hall) and Current Protocols in Cell Biology (2001, Bonifacino et al., Eds, John Wiley & Sons). A computer-readable storage medium of the invention, in combination with a programmable processor, may be used to coordinate the components necessary to monitor and maintain an active load on an organ or portion thereof.

In one embodiment, the weight of an organ or portion thereof may be entered into a computer-readable storage medium as described herein, which, in combination with a programmable processor, can calculate exposure times and perfusion pressures for that particular organ or tissue. Such a storage medium may record preload and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

The invention will be described by the following non-limiting example.

Example

Methods
Serum Harvest after Fifty Percent Hepatectomy

Animals used in this procedure are wild-type female large white pigs that weigh 25-30 kg. Animals first underwent a fifty-percent hepatectomy. The animal was sedated, intubated, and an intravenous catheter placed. She was placed supine on the operating table. A femoral arterial line was placed. The abdomen was prepped and draped in usual sterile fashion. A midline laparotomy was performed from xiphoid to 4 cm below umbilicus. The abdominal cavity was exposed using an Omni-Flex™ retractor. A cholecystectomy was performed and the liver was mobilized. The left lateral lobe of the liver was completely removed using Cavitron Ultrasonic Surgical Aspirator (CUSA). Portal veins, hepatic arteries, bile ducts, and hepatic veins were ligated with 2-0 silk. After the liver parenchyma was thinned out by CUSA, a long straight clamp was used to clamp across the remnant and the left lateral lobe was completely resected. The remnant was oversown by 3-0 Prolene. Similar techniques were used to resect half of the left medial and right medial lobe. The right lateral lobe was left intact. The abdomen was closed and the animal returned to recovery room. The animals are allowed to eat regular chow and drink as soon as they recovered.

48 hours later, the animal was returned to the operating room for serum harvest. Animal was sedated, intubated, and an intravenous catheter placed. The animal was placed supine and a femoral arterial line placed. The abdomen was prepped and draped in the usual sterile fashion. A 500 cc bolus of normal saline was given. The midline laparotomy incision was re-opened, and the incisions were extended laterally on both sides to make a cruciate incision. Abdominal contents were eviscerated to the left. The inferior vena cava (IVC) was exposed, then the infra-renal IVC was isolated and mobilized. The distal IVC was ligated, and a venotomy was made. Silicon tubing connected to a peristaltic pump was inserted and the tubing secured with 2-0 silk tie. The peristaltic pump was turned on and the phlebotomy began. At the end of the procedure, the whole blood is spun down in a centrifuge and serum collected.

Hepatocyte Seeding in a Perfusion Decellularized Liver

Whole perfusion decellularized livers were cannulated and perfused with cell culture media. Following an initial conditioning of 4-24 hours, the livers were seeded with 2 to 4 billion primary porcine hepatocytes through the hepatic vein and continually perfused at 12 to 20 mmHg. After 2 hours, perfusion was switched to the portal vein for the duration of the experiment and cell culture media was continuously perfused. Following 12 hours after the initial seeding, 0% (02H), 2% (03H), or 3% (04H) serum derived from a pig 48 hours following a 50% hepatectomy was added to the cell culture media and continuously perfused through the liver. The media was changed every 24-48 hours to replenish the media.

Histology

Histology staining with Ki67 demonstrate an increase in hepatocyte proliferation compared to the control.

Results

Liver cultures with 2% (03H) or 3% (04H) serum derived from a pig 48 hours following a 50% hepatectomy demonstrated about 2 to about 10× increase in albumin expression over the 14 days the culture was monitored, with a sustained high level of albumin expression levels in the 2% and 3% culture conditions compared to the 0% control.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method comprising contacting a substrate with:
   1) a plurality of cells comprising at least one hundred million primary hepatocytes, and
   2) an aqueous composition comprising 2% to 3% of blood or serum isolated from a mammal subjected to a liver resection, wherein the substrate comprises an at least partially decellularized isolated extracellular matrix of a liver or a portion thereof.

2. The method of claim 1 wherein the aqueous composition is prepared by collecting blood from the mammal subjected to the liver resection and isolating a serum fraction from the blood.

3. The method of claim 1 wherein the decellularized extracellular matrix is a human or porcine decellularized extracellular matrix.

4. The method of claim 1 wherein the function of the plurality of cells is enhanced by about 10% to about 1000% in the presence of the aqueous composition relative to the plurality of cells in the presence of the substrate but in the absence of the aqueous composition.

5. The method of claim 4 wherein albumin expression is enhanced.

6. The method of claim 1 wherein the plurality of cells further comprise cholangiocytes, endothelial cells, or stem cells.

7. The method of claim 1 wherein the substrate is perfused with media before the plurality of cells are contacted with the substrate or wherein the substrate is perfused with media after the plurality of cells are contacted with the substrate, or both.

8. The method of claim 7 wherein the media further comprises exogenously added activators or inhibitors of differentiation pathways selected to provide for liver-specific differentiation.

9. The method of claim 1 wherein the plurality of cells is contacted with the substrate by injection or perfusion, or a combination thereof.

10. The method of claim 1 wherein the plurality of cells contacted with the aqueous composition express albumin, express HepPar1, deposit glycogen, release albumin and urea, or any combination thereof.

11. The method of claim 1 wherein the plurality of cells are allogeneic or xenogeneic.

12. The method of claim 1 wherein the plurality of cells are human hepatocytes and the liver or the portion thereof is from a non-human mammal.

13. The method of claim 1 wherein the blood or serum is allogeneic or xenogeneic to the substrate or the plurality of cells.

* * * * *